US009701976B2

(12) United States Patent
Levering et al.

(10) Patent No.: US 9,701,976 B2
(45) Date of Patent: *Jul. 11, 2017

(54) ALFALFA PLANT AND SEED CORRESPONDING TO TRANSGENIC EVENT KK 179-2 AND METHODS FOR DETECTION THEREOF

(75) Inventors: Charlene Levering, St. Louis, MO (US); David Whalen, West Salem, WI (US); Stephen Temple, West Salem, WI (US); Mark McCaslin, Wet Salem, WI (US); Marry S. Reddy, Wet Salem, WI (US); William Hiatt, Rio Vista, CA (US); Wen C. Burns, Chesterfield, MO (US); Richard Eric Cerny, St. Louis, MO (US)

(73) Assignees: Monsanto Technology LLC, St. Louis, MO (US); Forage Genetics International LLC, West Salem, WI (US)

( * ) Notice: Subject to any disclaimer, the term of this patent is extended or adjusted under 35 U.S.C. 154(b) by 468 days.

This patent is subject to a terminal disclaimer.

(21) Appl. No.: 14/129,883

(22) PCT Filed: Jun. 28, 2012

(86) PCT No.: PCT/US2012/044590
§ 371 (c)(1),
(2), (4) Date: May 6, 2014

(87) PCT Pub. No.: WO2013/003558
PCT Pub. Date: Jan. 3, 2013

(65) Prior Publication Data
US 2014/0259227 A1 Sep. 11, 2014

Related U.S. Application Data

(60) Provisional application No. 61/664,359, filed on Jun. 26, 2012, provisional application No. 61/503,373, filed on Jun. 30, 2011.

(51) Int. Cl.
C12N 15/82 (2006.01)
A01H 5/12 (2006.01)
C12Q 1/68 (2006.01)

(52) U.S. Cl.
CPC .......... *C12N 15/8241* (2013.01); *A01H 5/12* (2013.01); *C12N 15/8255* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| 7,449,617 | B2 | 11/2008 | Dandekar et al. |
| 7,652,195 | B2 * | 1/2010 | Miller .................... A01H 5/10 435/410 |
| 7,663,023 | B2 | 2/2010 | Dixon et al. |
| 7,888,553 | B2 | 2/2011 | Dixon et al. |
| 2004/0049802 | A1 | 3/2004 | Dixon et al. |
| 2011/0229625 | A1 | 9/2011 | Hiatt et al. |
| 2012/0159664 | A1 | 6/2012 | Abad et al. |
| 2012/0272406 | A1 | 10/2012 | Guan et al. |
| 2015/0135370 | A1 | 5/2015 | Hiatt et al. |
| 2016/0090604 | A1 | 3/2016 | Hiatt |
| 2017/0067068 | A1 | 3/2017 | Levering et al. |

FOREIGN PATENT DOCUMENTS

| CA | 2 005 597 | | 6/1990 |
| CA | 2005597 | * | 6/1990 |
| WO | WO 01/73090 | | 10/2001 |
| WO | WO 2004/070020 | | 8/2004 |
| WO | WO 2006/012594 | | 2/2006 |
| WO | WO 2013-003558 | | 1/2013 |

OTHER PUBLICATIONS

Undersander et al, Proceedings, 2009 Western Alfalfa & Forage Conference, Dec. 2-4, 2009, Reno, Nevada. Published by: UC Cooperative Extension, Plant Sciences Department, University of California, Davis 95616.*
Rusch et al, 2010, GenBank Accession ER325305.*
Neafsey et al, 2008, GenBank: Accession GH365427.*
Fang et al., "Multi-site genetic modulation of monolignol biosynthesis suggests new routes for formation of syringyl lignin and wall-bound ferulic acid in alfalfa (*Medicago sativa* L.)," *Plant J* 48(1):113-124, 2006.
Guo et al., "Downregulation of caffeic acid 3-O-Methyltransferase and caffeoyl 3-O-Methyltransferase in transgenic alfalfa: impacts on lignin structure and implications for the biosynthesis of G and S lignin," *Plant Cell* 13(1):73-88, 2001.
Guo et al., "Improvement of in-rumen digestibility of alfalfa forage by genetic manipulation of lignin O-methyltransferases," *Transgenic Res* 10(5):457-464, 2001.
International Search Report issued in PCT/US2012/044590, dated Oct. 9, 2012.
Marita et al., "Structural and compositional modifications in lignin of transgenic alfalfa down-regulated in caffeic acid 3-O-methyltransferase and caffeoyl coenzyme A 3-O-methyltransferase," *Phytochem* 62(1):53-65, 2003.

(Continued)

*Primary Examiner* — Anne Kubelik
(74) *Attorney, Agent, or Firm* — Dentons US LLP

(57) ABSTRACT

The present invention provides a transgenic alfalfa event KK 179-2. The invention also provides cells, plant parts, seeds, plants, commodity products related to the event, and DNA molecules that are unique to the event and were created by the insertion of transgenic DNA into the genome of a alfalfa plant. The invention further provides methods for detecting the presence of said alfalfa event nucleotide sequences in a sample, probes and primers for use in detecting nucleotide sequences that are diagnostic for the presence of said alfalfa event.

10 Claims, 1 Drawing Sheet

(56) References Cited

OTHER PUBLICATIONS

Mumm et al., "Quality control in the development of transgenic crop seed products," *Crop Sci* 41:1381-1389, 2001.
Reisen et al., "Roundup ready alfalfa update and new biotech traits," 2009 WSHGA Annual Conference Proceedings, pp. 1-9, Jan. 1, 2009.
Taverniers et al., "Event-specific plasmid standards and real-tinie PCR methods for transgenic Bt11, Bt176, and GA21 maize and transgenic GT73 canola," J Agric Food Chem 53:3041-3052, 2005.
Undersander, "Low-lignin alfalfa: redefining the yield/quality tradeoff," 2009 Western Alfalfa & Forage Conference, Alfalfa Leaf Image "Improving your odds of Profitability," Dec. 1, 2009.
Visarada et al., "Transgenic breeding: perspectives and prospects," *Crop Sci* 49(5):1555-1563, 2009.
Getachew et al., "Impacts of polyphenol oxidase enzyme expression in transgenic alfalfa on in vitro gas production and ruminal degration of protein, and nitrogen release during ensiling," *Animal Feed Sci. Tech.*, 151:44-54, 2009.
Sullivan et al., "Polyphenol oxidase and o-diphernois inhibit post-harvest proteolysis of red clover and alfalfa," *Crop Sci.*, 46(2):662-670, 2006.
Carleton et al., "Seed Size Effects Upon Seedling Vigor of Three Forage Legumes," *Crop Science* 12(2):183-186, abstract, 1972.
Jung et al., "Correlation of Acid Detergent Lignin and Klason Lignin with Digestibility of Forage Dry Matter and Neutral Detergent Fiber," *Journal of Dairy Science* 80:1622-1628, 1997.
International Search Report and Written Opinion for International Application No. PCT/US2013/047911, dated Mar. 3, 2014.
Hans-Joachim et al., "Modifying crops to increase cell wall digestibility," *Plant Science* 185-186:65-77, 2012.
Hatfield et al., "Can Lignin Be Accurately Measured?," *Crop Science* 45:832-839, 2005.
Jung et al., "Cell wall composition and degradability of stem tissue from lucerne divergently selected for lignin and in vitro dry-matter disappearance," *Grass and Forage Science* 49:295-304, 1994.
Riday et al., "Progress Report on Reduced-Lignin Alfalfa: Part I, Plant Modifications," *Forage Focus—USDA-ARS*, May 2009.
Extended European Search Report regarding European Application No. EP 13 80 8555, dated Feb. 16, 2016.
GenBank Accession No. U20736, dated Aug. 7, 1998.
Inoue et al., "Developmental Expression and Substrate Specificities of Alfalfa Caffeic Acid 3-O-Methyltransferase and Caffeoyl Coenzyme A 3-O-Methyltransferase in Relation to Licinification," *Plant Physiol.* 117:761-770, 1998.
U.S. Appl. No. 15/356,348, filed Nov. 18, 2016, Levering et al.
USPTO: Non-Final Office Action regarding U.S. Appl. No. 15/356,348, dated Dec. 19, 2016.
Response to Non-Final Office Action regarding U.S. Appl. No. 15/356,348, dated Feb. 17, 2017.
USPTO: Final Office Action regarding U.S. Appl. No. 15/356,348, dated Mar. 15, 2017.
Response to Final Office Action regarding U.S. Appl. No. 15/356,348, dated Mar. 29, 2017.
USPTO: Notice of Allowance and Fees due regarding U.S. Appl. No. 15/356,348, dated Apr. 5, 2017.
USPTO: Final Office Action regarding U.S. Appl. No. 13/029,500, dated Apr. 12, 2017.
USPTO: Non-Final Office Action regarding U.S. Appl. No. 14/885,530, dated Apr. 12, 2017.

\* cited by examiner

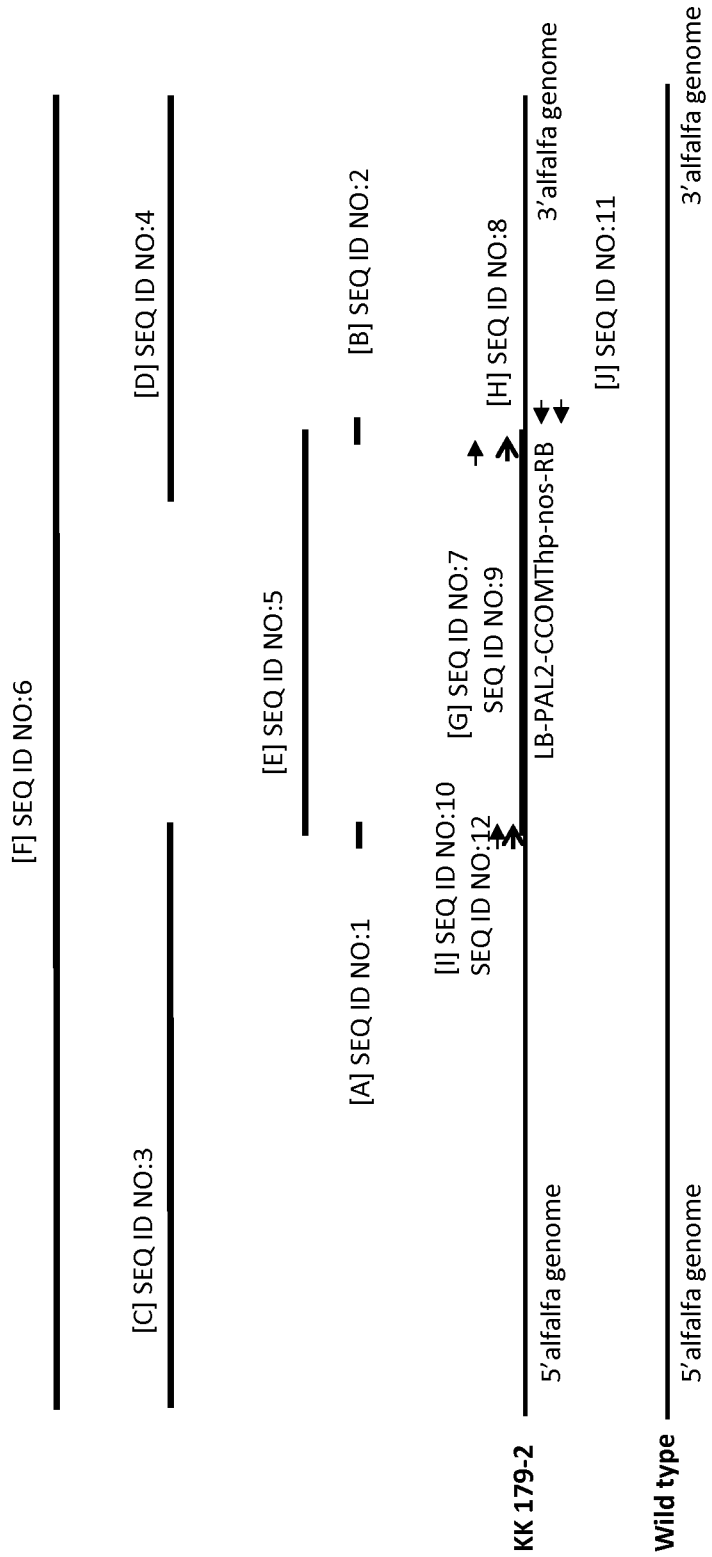

ALFALFA PLANT AND SEED CORRESPONDING TO TRANSGENIC EVENT KK 179-2 AND METHODS FOR DETECTION THEREOF

CROSS-REFERENCE TO RELATED APPLICATIONS

This application is a 371 National Stage application of International Application No. PCT/US2012/044590, filed Jun. 28, 2012, which is entitled to priority pursuant to 35 U.S.C. §119 (e) to U.S. provisional patent application No. 61/503,373, which was filed on Jun. 30, 2011, and U.S. provisional patent application No. 61/664,359, which was filed on Jun. 26, 2012, the disclosures of which are incorporated by reference in their entirety.

INCORPORATION OF SEQUENCE LISTING

The sequence listing file named "57978_seq_listing.txt", which is 10,564 bytes (measured in MS-WINDOWS) which was electronically filed and which was created on May 1, 2012 is incorporated herein by reference.

FIELD OF THE INVENTION

The present invention relates to alfalfa transgenic event KK179-2. The invention also provides cells, plant parts, seeds, plants, commodity products related to the event, and DNA molecules that are unique to the event and were created by the insertion of transgenic DNA into the genome of an alfalfa plant. The invention further provides methods for detecting the presence of said alfalfa event nucleotide sequences in a sample, probes and primers for use in detecting nucleotide sequences that are diagnostic for the presence of said alfalfa event.

BACKGROUND OF THE INVENTION

Alfalfa (*Medicago sativa*) is the most cultivated legume worldwide, with the US being the top alfalfa producer. The methods of biotechnology have been applied to alfalfa for improvement of agronomic traits and the quality of the product. One such agronomic trait is lignin content.

Lignin is the second most abundant terrestrial biopolymer and accounts for 30% of the organic carbon. Lignin is crucial for structural integrity of the cell wall and it imparts stiffness and strength to the stem. Lignin content is inversely correlated with forage digestibility for diary cattle. A reduction in lignin may be achieved in transgenic plants by the expression of a RNA suppression construct capable of providing such decrease while at the same time provide increased alfalfa digestibility. The expression of foreign genes or suppression molecules in plants is known to be influenced by many factors, such as the regulatory elements used, the chromosomal location of the transgene insert, the proximity of any endogenous regulatory elements close to the transgene insertion site, and environmental factors such as light and temperature. For example, it has been observed that there may be variation in the overall level of transgene suppression or in the spatial or temporal pattern of transgene suppression between similarly-produced events. For this reason, it is often necessary to screen hundreds of independent transformation events in order to ultimately identify one event useful for commercial agricultural purposes. Such an event, once identified as having the desired suppression phenotype, molecular characteristics and the improved trait, may then be used for introgressing the improved trait into other genetic backgrounds using plant breeding methods. The resulting progeny would contain the transgenic event and would therefore have the same characteristics for that trait of the original transformant. This may be used to produce a number of different crop varieties that comprise the improved trait and are suitably adapted to specific local growing conditions.

It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the transgenic crop plants.

The presence or absence of a suppression element may be detected by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different transformation events, particularly those produced using the same DNA construct unless the sequence of chromosomal DNA adjacent to the inserted DNA ("flanking DNA") is known. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event GT73 was demonstrated. In this study, event-specific primers and probes were designed based upon the sequences of the genome/transgene junctions for each event. Transgenic plant event specific DNA detection methods have also been described in U.S. Pat. Nos. 7,632,985; 7,566,817; 7,368,241; 7,306,909; 7,718,373; 7,189,514, 7,807,357 and 7,820,392.

SUMMARY OF THE INVENTION

The present invention is an alfalfa transgenic event designated event KK179-2, having representative seed sample deposited with American Type Culture Collection (ATCC) under the Accession No. PTA-11833.

The invention provides a plant, seed, cell, progeny plant, or plant part comprising the event derived from a plant, cell, plant part, or seed comprising event KK179-2. The invention thus includes, but is not limited to pollen, ovule, flowers, shoots, roots and leaves.

One aspect of the invention provides compositions and methods for detecting the presence of a DNA transgenic/genomic junction region from alfalfa event KK179-2 plant or seed. DNA molecules are provided that comprise at least one transgene/genomic junction DNA molecule selected from the group consisting of SEQ ID NO: 1, SEQ ID NO: 2 and complements thereof, wherein the junction molecule spans the insertion site. An alfalfa event KK179-2 and seed comprising these DNA molecules is an aspect of this invention.

A novel DNA molecule is provided that is a DNA transgene/genomic region SEQ ID NO:3 or the complement thereof, from alfalfa event KK179-2. An alfalfa plant and seed comprising SEQ ID NO: 3 in its genome is an aspect of this invention. In another aspect of the invention, a DNA molecule is provided that is a DNA transgene/genomic resion SEQ ID NO:4 or the complement thereof, wherein this DNA molecule is novel in alfalfa event KK179-2. An alfalfa plant and seed comprising SEQ ID NO:4 in its genome is an aspect of this invention.

The invention provides DNA molecules related to event KK179-2. These DNA molecules may comprise nucleotide sequences representing or derived from the junction of the transgene insertion and flanking genomic DNA of event KK179-2, and/or a region of the genomic DNA flanking the inserted DNA, and/or a region of the integrated transgenic DNA flanking the insertion site, and/or a region of the integrated transgenic expression cassette, and/or a contiguous sequence of any of these regions. The invention also provides DNA molecules useful as primers and probes diagnostic for the event. Plants, cells, plant parts, commodity products, progeny, and seeds comprising these molecules are provided.

According to one aspect of the invention, compositions and methods are provided for detecting the presence of the transgene/genomic insertion region from a novel alfalfa plant designated KK179-2. DNA sequences are provided that comprise at least one junction sequence of KK179-2 selected from the group consisting of SEQ ID NO: 1 (corresponding to positions 1038 through 1057 of SEQ ID NO: 6, FIG. 1 [F]), and SEQ ID NO: 2 (corresponding to positions 3620 through 3639 of SEQ ID NO: 6, FIG. 1 [F]), and complements thereof; wherein a junction sequence is a nucleotide sequence that spans the point at which heterologous DNA inserted into the genome is linked to the alfalfa cell genomic DNA and detection of this sequence in a biological sample containing alfalfa DNA is diagnostic for the presence of the alfalfa event KK179-2 DNA in said sample (FIG. 1). The alfalfa event KK179-2 and alfalfa seed comprising these DNA molecules is an aspect of this invention.

According to another aspect of the invention, two DNA molecules are provided for use in a DNA detection method, wherein a first DNA molecule comprises a polynucleotide having a nucleotide sequence of sufficient length of consecutive polynucleotide of any portion of the transgene region of the DNA molecule of SEQ ID NO: 3 or SEQ ID NO: 5 and a second DNA molecule of similar length of any portion of a 5' flanking alfalfa genomic DNA region of SEQ ID NO: 3, where said DNA molecules function as DNA primers when used together in an amplification reaction with a template derived from event KK179-2 to produce an amplicon diagnostic for event KK179-2 DNA in a sample. Any amplicon produced by DNA primers homologous or complementary to any portion of SEQ ID NO: 3 and SEQ ID NO: 5, and any amplicon that comprises SEQ ID NO: 1 is an aspect of the invention.

According to another aspect of the invention, two DNA molecules are provided for use in a DNA detection method, wherein a first DNA molecule comprises a polynucleotide having a nucleotide sequence of sufficient length of consecutive polynucleotide of any portion of the transgene region of the DNA molecule of SEQ ID NO: 4 or SEQ ID NO: 5 and a second DNA molecule of similar length of any portion of a 3' flanking alfalfa genomic DNA of SEQ ID NO: 4, where said DNA molecules function as DNA primers when used together in an amplification reaction with a template derived from event KK179-2 to produce an amplicon diagnostic for event KK179-2 DNA in a sample. Any amplicons produced by DNA primers homologous or complementary to any portion of SEQ ID NO: 4 and SEQ ID NO: 5, and any amplicon that comprises SEQ ID NO: 2 is an aspect of the invention.

The invention provides methods, compositions, and kits useful for detecting the presence of DNA derived from alfalfa event KK179-2. Certain methods comprise (a) contacting a sample comprising DNA with a primer set that when used in a nucleic acid amplification reaction with genomic DNA from alfalfa event KK179-2 produces an amplicon diagnostic for the event; (b) performing a nucleic acid amplification reaction thereby producing the amplicon; and (c) detecting the amplicon, wherein said amplicon comprises SEQ ID NO: 1 and/or SEQ ID NO: 2. The invention also provides a method for detection of the event by (a) contacting a sample comprising DNA with a probe that when used in a hybridization reaction with genomic DNA from the event hybridizes to a DNA molecule specific for the event; (b) subjecting the sample and probe to stringent hybridization conditions; and (c) detecting the hybridization of the probe to the DNA molecule. Kits comprising the methods and compositions of the invention useful for detecting the presence of DNA derived from the event are also provided.

The invention further provides a method of producing a alfalfa plant comprising: (a) crossing a KK179-2 alfalfa plant with a second alfalfa plant, thereby producing a seed; (b) growing said seed to produce a plurality of progeny plants; and (c) selecting a progeny plant that comprises KK179-2 or a progeny plant with decreased lignin content.

The foregoing and other aspects of the invention will become more apparent from the following detailed description.

BRIEF DESCRIPTION OF THE DRAWINGS

FIG. 1. Diagrammatic representation of the transgenic insert in the genome of alfalfa event KK179-2; [A] corresponds to the relative positions of SEQ ID NO: 1 forming the junction between SEQ ID NO: 3 and SEQ ID NO: 5; [B] corresponds to the relative positions of SEQ ID NO: 2 forming the junction between SEQ ID NO: 4 and SEQ ID NO: 5; [C] corresponds to the relative position of SEQ ID NO: 3, which contains the alfalfa genomic flanking region and a portion of the arbitrarily designated 5' end of the transgenic DNA insert; [D] corresponds to the relative position of SEQ ID NO: 4, which contains the alfalfa genome flanking region and a portion of the arbitrarily designated 3' end of the transgenic DNA insert; [E] represents SEQ ID NO: 5, which is the sequence of the transgenic DNA insert including the CCOMT suppression cassette integrated into the genome of event KK179-2; [F] represents SEQ ID NO: 6, which is the contiguous sequence comprising, as represented in the figure from left to right, SEQ ID NO: 3, SEQ ID NO: 5 and SEQ ID NO: 4, in which SEQ ID NOs: 1 and SEQ ID NOs: 2 are incorporated as set forth above, as these sequences are present in the genome in event KK179-2. LB: refers to the left border of T-DNA; RB: refers to the right border of T-DNA.

BRIEF DESCRIPTION OF THE SEQUENCES

The sequence listing file named "57978_seq_listing.txt", which is 10,564 bytes (measured in MS-WINDOWS) which was electronically filed and which was created on May 1, 2012 is incorporated herein by reference.

SEQ ID NO: 1—A 20 bp nucleotide sequence representing the left border junction between the alfalfa genomic DNA and the integrated DNA insert. This sequence corresponds to positions 1038 through 1057 of SEQ ID NO: 6, and to positions 1038 through 1047 of SEQ ID NO: 3 ([C] of FIG. 1). In addition, SEQ ID NO: 1 corresponds to the integrated left border of the expression cassette at positions 1 through 10 of SEQ ID NO: 5 ([E] of FIG. 1).

SEQ ID NO: 2—A 20 bp nucleotide sequence representing the right border junction between the integrated DNA insert and the alfalfa genomic DNA. This sequence corresponds to positions 3620 to 3639 of SEQ ID NO: 6, and to positions 91 through 111 of SEQ ID NO: 4 ([D] of FIG. 1). In addition, SEQ ID NO: 2 corresponds to positions 2573 through 2582 SEQ ID NO: 5 ([E] of FIG. 1).

SEQ ID NO: 3—A 1147 bp nucleotide sequence including the 5' alfalfa genomic sequence (1047 bp) flanking the inserted DNA of event KK179-2 plus a region (100 bp) of the integrated DNA. This sequence corresponds to positions 1 through 1047 of SEQ ID NO: 6.

SEQ ID NO: 4—A 1356 bp nucleotide sequence including the 3' alfalfa genomic sequence (1256 bp) flanking the inserted DNA of event KK179-2 plus a region (100 bp) of the integrated DNA. This sequence corresponds to positions 3529 through 4885 of SEQ ID NO: 6.

SEQ ID NO: 5—The sequence of the integrated expression cassette, including the left and the right border sequences after integration. SEQ ID NO: 5 corresponds to nucleotide positions 1048 through 3629 of SEQ ID NO: 6.

SEQ ID NO: 6—A 4885 bp nucleotide sequence representing the contig of the 5' sequence flanking the inserted DNA of KK179-2 (SEQ ID NO: 3), the sequence of the integrated DNA insert (SEQ ID NO: 5) and the 3' sequence flanking the inserted DNA of KK179-2 (SEQ ID NO: 4).

SEQ ID NO: 7—The sequence of primer SQ20901 used to identify KK179-2 event. Production of a 81 bp PCR amplicon using the combination of primers SQ20901 and SQ23728 (SEQ ID NO: 8) is a positive result for the presence of event KK179-2.

SEQ ID NO 8—The sequence of primer SQ223728 used to identify KK179-2 event.

SEQ ID NO: 9—The sequence of probe PB10164 used to identify KK179-2 event. It is a 6FAM™-labeled synthetic oligonucleotide.

SEQ ID NO: 10—The sequence of primer SQ1532 used as an internal control in end-point TAQMAN® assays.

SEQ ID NO: 11—The sequence of primer SQ1533 used as an internal control in end-point TAQMAN® assays.

SEQ ID NO: 12—The sequence of a VIC™-labeled synthetic oligonucleotide probe PB0359 used as an internal control in end-point TAQMAN® assays.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

The present invention provides transgenic alfalfa event KK179-2. The term "event" as used herein refers to the plants, seeds, progeny, cells, plant parts thereof, and DNA molecules produced as a result of transgenic DNA integration into a plant's genome at a particular location on a chromosome. Event KK179-2 refers to the plants, seeds, progeny, cells, plant parts thereof, and DNA molecules produced as a result of the insertion of transgenic DNA having a sequence provided herein as SEQ ID NO: 5 into a particular chromosomal location in the *Medicago sativa* genome. A seed sample containing KK179-2 has been deposited with American Type Culture Collection (ATCC) under Accession No. PTA-11833.

As used herein, the term "alfalfa" means *Medicago sativa* and includes all plant varieties that can be bred with alfalfa, including wild alfalfa species. Alfalfa is also called medic, the name of any plant of the genus *Medicago* Old World herbs with blue or yellow flowers similar to those of the related clovers. Unlike corn or soybean, alfalfa plants are autotetraploid; thus, each trait is determined by genes residing on four chromosomes instead of two. This complicates genetic research and also adds to the difficulty of improving alfalfa. Commercial alfalfa seed is often comprised of a mixture of clones that may constitute a synthetic cultivar generated by random interpollination among the selected clones, followed by one to three generations of open-pollination in isolation. Additionally, a composite cultivar of alfalfa may also be developed by blending see of two or more clones or interpollinating clones in isolation. When forming a composite cultivar, equal quantities of seed from each component clone would be blended to form the initial breeder seed stock.

A transgenic "event" is produced by transformation of plant cells with heterologous DNA, such as, a nucleic acid construct that comprises the RNA suppression of a gene of interest, regeneration of a population of independently transformed transgenic plants resulting from the insertion of the transgene cassette into the genome of the plant, and selection of a particular plant with desirable molecular characteristics, such as insertion of the transgene into a particular genome location. A plant comprising the event can refer to the original transformant that includes the transgene inserted into the particular location in the plant's genome. A plant comprising the event can also refer to progeny of the original transformant that retain the transgene at the same particular location in the plant's genome. Such progeny may be produced by a sexual outcross between the transformant, or its progeny, and another plant. Such another plant may be a transgenic plant comprising the same or a different transgene; or may be a non-transgenic plant, such as one from a different variety. Even after repeated back-crossing to a recurrent parent, the event DNA from the transformed parent is present in the progeny of the cross at the same genomic location.

A DNA molecule comprising event KK179-2 refers to a DNA molecule comprising at least a portion of the inserted transgenic DNA (provided as SEQ ID NO: 5) and at least a portion of the flanking genomic DNA immediately adjacent to the inserted DNA. As such, a DNA molecule comprising event KK179-2 has a nucleotide sequence representing at least a portion of the transgenic DNA insert and at least a portion of the particular region of the genome of the plant into which the transgenic DNA was inserted. The arrangement of the inserted DNA in event KK179-2 in relation to the surrounding plant genome is specific and unique to event KK179-2 and as such the nucleotide sequence of such a DNA molecule is diagnostic and identifying for event KK179-2. Examples of the sequence of such a DNA molecule are provided herein as SEQ ID NO: 1, SEQ ID NO: 2, SEQ ID NO: 3, SEQ ID NO: 4, and SEQ ID NO: 6. Such a DNA molecule is also an integral part of the chromosome of a plant that comprises event KK179-2 and may be passed on to progenies of the plant.

As used herein, a "recombinant DNA molecule" is a DNA molecule comprising a combination of DNA molecules that would not naturally occur together and is the result of human intervention, for example, a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the *Medicago sativa* genome, which may ultimately result in the suppression of a recombinant RNA and/or protein molecule in that organism. The nucleotide sequence or any fragment derived therefrom would also be considered a recombinant DNA molecule if the DNA molecule can be extracted from cells, or tissues, or homogenate from a plant or seed or plant tissue; or can be produced as an amplicon from extracted DNA or RNA from cells, or tissues, or homogenate from a plant or seed or plant tissue, any of which is derived from such materials derived from the event KK179-2. For that matter, the junction sequences as set forth at SEQ ID NO: 1 and SEQ ID NO: 2, and nucleotide sequences derived from event KK179-2 that also contain these junction sequences are considered to be recombinant DNA, whether these sequences are present within the genome of the cells of event KK179-2 or present in detectable amounts in tissues, progeny, biological samples or commodity products derived from the event KK179-2. As used herein, the term "transgene" refers to a polynucleotide molecule artificially incorporated into a host cell's genome. Such transgene may be heterologous to the host cell. The term "transgenic plant" refers to a plant comprising such a transgene. A "transgenic plant" includes a plant, plant part, a plant cell or seed whose genome has been altered by the stable integration of recombinant DNA. A transgenic plant includes a plant regenerated from an originally-transformed plant cell and progeny transgenic plants from later generations or crosses of a transformed plant. As a result of such genomic alteration, the transgenic plant is distinctly different from the related wild type plant. An example of a transgenic plant is a plant described herein as comprising event KK179-2.

As used herein, the term "heterologous" refers to a sequence which is not normally present in a given host genome in the genetic context in which the sequence is currently found. In this respect, the sequence may be native to the host genome, but be rearranged with respect to other genetic sequences within the host sequence.

The present invention provides DNA molecules and their corresponding nucleotide sequences. As used herein, the terms "DNA sequence", "nucleotide sequence" and "polynucleotide sequence" refer to the sequence of nucleotides of a DNA molecule, usually presented from the 5' (upstream) end to the 3' (downstream) end. The nomenclature used herein is that required by Title 37 of the United States Code of Federal Regulations §1.822 and set forth in the tables in WIPO Standard ST.25 (1998), Appendix 2, Tables 1 and 3. The present invention is disclosed with reference to only one strand of the two nucleotide sequence strands that are provided in transgenic event KK179-2. Therefore, by implication and derivation, the complementary sequences, also referred to in the art as the complete complement or the reverse complementary sequences, are within the scope of the present invention and are therefore also intended to be within the scope of the subject matter claimed.

The nucleotide sequence corresponding to the complete nucleotide sequence of the inserted transgenic DNA and substantial segments of the *Medicago sativa* genomic DNA flanking either end of the inserted transgenic DNA is provided herein as SEQ ID NO: 6. A subsection of this is the inserted transgenic DNA provided as SEQ ID NO: 5. The nucleotide sequence of the genomic DNA flanking the 5' end of the inserted transgenic DNA and a portion of the 5' end of the inserted DNA is provided herein as SEQ ID NO: 3. The nucleotide sequence of the genomic DNA flanking the 3' end of the inserted transgenic DNA and a portion of the 3' end of the inserted DNA is provided herein as SEQ ID NO: 4. The region spanning the location where the transgenic DNA connects to and is linked to the genomic DNA is referred to herein as the junction. A "junction sequence" or "junction region" refers to a DNA sequence and/or corresponding DNA molecule that spans the inserted transgenic DNA and the adjacent flanking genomic DNA. Examples of a junction sequence of event KK179-2 are provided herein as SEQ ID NO: 1 and SEQ ID NO: 2. The identification of one of these junction sequences in a nucleotide molecule derived from a alfalfa plant or seed is conclusive that the DNA was obtained from event KK179-2 and is diagnostic for the presence of DNA from event KK179-2. SEQ ID NO: 1 is a 20 bp nucleotide sequence spanning the junction between the genomic DNA and the 5' end of the inserted DNA. SEQ ID NO: 2 is a 20 bp nucleotide sequence spanning the junction between the genomic DNA and the 3' end of the inserted DNA. Any segment of DNA derived from transgenic event KK179-2 that includes the consecutive nucleotides of SEQ ID NO: 1 is within the scope of the present invention. Any segment of DNA derived from transgenic event KK179-2 that includes the consecutive nucleotides of SEQ ID NO: 2 is within the scope of the present invention. In addition, any polynucleotide molecule comprising a sequence complementary to any of the sequences described within this paragraph is within the scope of the present invention. FIG. 1 is an illustration of the transgenic DNA insert in the genome of alfalfa event KK179-2, and the relative positions of SEQ ID NOs: 1-6 arranged 5' to 3'.

The present invention further provides exemplary DNA molecules that can be used either as primers or probes for diagnosing the presence of DNA derived from event KK179-2 in a sample. Such primers or probes are specific for a target nucleic acid sequence and as such are useful for the identification of event KK179-2 nucleic acid sequence by the methods of the invention described herein.

A "probe" is an isolated nucleic acid to which is attached a detectable label or reporter molecule, for example, a radioactive isotope, ligand, chemiluminescent agent, or enzyme. Such a probe is complementary to a strand of a target nucleic acid, in the case of the present invention, to a strand of genomic DNA from alfalfa event KK179-2 whether from a alfalfa plant or from a sample that comprises DNA from the event. Probes according to the present invention include not only deoxyribonucleic or ribonucleic acids but also polyamides and other probe materials that bind specifically to a target DNA sequence and the detection of such binding can be used to diagnose/determine/confirm the presence of that target DNA sequence in a particular sample.

A "primer" is typically an isolated polynucleotide that is designed for use in specific annealing or hybridization methods to hybridize to a complementary target DNA strand to form a hybrid between the primer and the target DNA strand, and then extended along the target DNA strand by a polymerase, for example, a DNA polymerase. A pair of primers may be used with template DNA, such as a sample of *Medicago sativa* genomic DNA, in a thermal or isothermal amplification, such as polymerase chain reaction (PCR), or other nucleic acid amplification methods, to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques, such as the product of an amplification reaction. In one embodiment of the invention, an amplicon diagnostic for event KK179-2 comprises a sequence not naturally found in the *Medicago sativa* genome. Primer pairs, as used in the present invention, are intended to refer to use of two primers binding opposite strands of a double stranded nucleotide segment for the purpose of amplifying linearly the polynucleotide segment between the positions targeted for binding by the individual members of the primer pair, typically in a thermal or isothermal amplification reaction or other nucleic acid amplification methods. Exemplary DNA molecules useful as primers are provided as SEQ ID NOs: 7-9, may be used as a first DNA molecule and a second DNA molecule that is different from the first DNA molecule, and both molecules are each of sufficient length of consecutive nucleotides of either SEQ ID NO: 4, SEQ ID NO: 5, or SEQ ID NO: 6 or the complements thereof to function as DNA primers so that, when used together in an amplification reaction with template DNA derived from event KK179-2, an amplicon that is specific and unique to transgenic event KK179-2 would be produced. The use of the term "amplicon" specifically excludes primer-dimers that may be formed in the DNA amplification reaction.

Probes and primers according to the present invention may have complete sequence identity to the target sequence, although primers and probes differing from the target sequence that retain the ability to hybridize preferentially to target sequences may be designed by conventional methods. In order for a nucleic acid molecule to serve as a primer or probe it needs only be sufficiently complementary in sequence to be able to form a stable double-stranded structure under the particular solvent and salt concentrations employed. Any nucleic acid hybridization or amplification method can be used to identify the presence of transgenic DNA from event KK179-2 in a sample. Probes and primers are generally at least about 11 nucleotides, at least about 18 nucleotides, at least about 24 nucleotides, and at least about 30 nucleotides or more in length. Such probes and primers hybridize specifically to a target sequence under high stringency hybridization conditions.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, Whitehead Institute for Biomedical Research, Cambridge, Mass.).

Primers and probes based on the flanking DNA and insert sequences disclosed herein can be used to confirm the disclosed sequences by known methods, for example, by re-cloning and sequencing such sequences.

The nucleic acid probes and primers of the present invention hybridize under stringent conditions to a target DNA sequence. Any nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least "low-stringency" conditions. Similarly, the molecules are said to be "complementary" if they can hybridize to one another with sufficient stability to permit them to remain annealed to one another under "high-stringency" conditions. Stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In one embodiment, a nucleic acid of the present invention will specifically hybridize to one or more of the nucleic acid molecules set forth in SEQ ID NO: 1, and SEQ ID NO: 2, or complements or fragments thereof under high stringency conditions. The hybridization of the probe to the target DNA molecule can be detected by any number of methods known to those skilled in the art. These can include, but are not limited to, fluorescent tags, radioactive tags, antibody based tags, and chemiluminescent tags.

Regarding the amplification of a target nucleic acid sequence (for example, by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA amplification reaction. Examples of DNA amplification methods include PCR, Recombinase Polymerase Amplification (RPA) (see for example U.S. Pat. No. 7,485,428), Strand Displacement Amplification (SDA) (see for example, U.S. Pat. Nos. 5,455,166 and 5,470,723), Transcription-Mediated Amplification (TMA) (see for example, Guatelli et al., *Proc. Natl. Acad. Sci. USA* 87:1874-1878 (1990)), Rolling Circle Amplification (RCA) (see for example, Fire and Xu, *Proc. Natl. Acad Sci. USA* 92:4641-4645 (1995); Lui, et al., *J. Am. Chem. Soc.* 118:1587-1594 (1996); Lizardi, et al., *Nature Genetics* 19:225-232 (1998), U.S. Pat. Nos. 5,714,320 and 6,235,502)), Helicase Dependant Amplification (HDA) (see for example Vincent et al., *EMBO Reports* 5(8): 795-800 (2004); U.S. Pat. No. 7,282,328), and Multiple Displacement Amplification (MDA) (see for example Dean et. al., *Proc. Natl. Acad Sci. USA* 99:5261-5266 (2002)).

The term "specific for (a target sequence)" indicates that a probe or primer hybridizes under stringent hybridization conditions only to the target sequence in a sample comprising the target sequence.

As used herein, the term "isolated" refers to at least partially separating a molecule from other molecules normally associated with it in its native or natural state. In one embodiment, the term "isolated" refers to a DNA molecule that is at least partially separated from the nucleic acids that normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying event KK179-2, selecting plant varieties or hybrids comprising event KK179-2, detecting the presence of DNA derived from event KK179-2 in a sample, and monitoring samples for the presence and/or absence of event KK179-2 or plants and plant parts comprising event KK179-2.

The present invention provides plants, progeny, seeds, plant cells, plant parts such as pollen, ovule, pod, flower, root or stem tissue, and leaf. These plants, progeny, seeds, plant cells, plant parts, and commodity products contain a detectable amount of a polynucleotide of the present invention, such as a polynucleotide comprising at least one of the sequences provided as the consecutive nucleotides of SEQ ID NO: 1, and the consecutive nucleotides of SEQ ID NO: 2. Plants, progeny, seeds, plant cells, plant parts and commodity products of the present invention may also contain one or more additional suppression targets.

The present invention provides plants, progeny, seeds, plant cells, and plant part such as pollen, ovule, pod, flower, root or stem tissue, and leaf derived from a transgenic plant comprising event KK179-2. A representative sample of seed comprising event KK179-2 has been deposited according to the Budapest Treaty for the purpose of enabling the present invention. The repository selected for receiving the deposit is the American Type Culture Collection (ATCC) having an address at 10801 University Boulevard, Manassas, Va. USA, Zip Code 20110. The ATCC repository has assigned the accession No. PTA-11833 to event KK179-2 seed.

The present invention provides a microorganism comprising a DNA molecule having a nucleotide sequence selected from the group consisting of the consecutive nucleotides of SEQ ID NO: 1, the consecutive nucleotides of SEQ ID NO: 2. An example of such a microorganism is a transgenic plant cell. Microorganisms, such as a plant cell of the present invention, are useful in many industrial applications, including but not limited to: (i) use as research tool for scientific inquiry or industrial research; (ii) use in culture for producing endogenous or recombinant carbohydrate, lipid, nucleic acid, enzymes or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the present invention is a method of using a microorganism of the present invention. Methods of using microorganisms of the present invention, such as transgenic plant cells, include (i) methods of producing transgenic cells by integrating recombinant DNA into genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, enzymes or protein products from cultured cells; and (iv) methods of using modern plant tissue culture techniques with transgenic plant cells to produce transgenic plants or transgenic plant tissue cultures.

As used herein, "progeny" includes any plant, seed, plant cell, and/or regenerable plant part comprising the event DNA derived from an ancestor plant and/or a polynucleotide having at least one of the sequences provided as the consecutive nucleotides of SEQ ID NO: 1 or the consecutive nucleotides of SEQ ID NO: 2. Plants, progeny, and seeds may heterozygous for the presence of the transgenic sequence. Progeny may be grown from seeds produced by a plant comprising event KK179-2 and/or from seeds produced by a plant fertilized with pollen from a plant comprising event KK179-2.

Progeny plants may be outcrossed, for example, bred with another plant, to produce a varietal or a hybrid seed or plant. The other plant may be transgenic or nontransgenic. A varietal or hybrid seed or plant of the present invention may thus be derived by crossing a first parent that lacks the specific and unique DNA of event KK179-2 with a second parent comprising event KK179-2, resulting in a hybrid comprising the specific and unique DNA of event KK179-2. Each parent can be a hybrid or an inbred/variety, so long as the cross or breeding results in a plant or seed of the present invention, such as, a seed having at least one allele comprising the specific and unique DNA of event KK179-2 and/or the consecutive nucleotides of SEQ ID NO: 1 or SEQ ID NO: 2. Back-crossing to a parental plant and out-crossing with a non-transgenic plant are also contemplated, as is vegetative propagation. Descriptions of other breeding methods that are commonly used for different traits and crops can be found in one of several references, for example, Fehr, in *Breeding Methods for Cultivar Development*, Wilcox J. ed., American Society of Agronomy, Madison Wis. (1987).

Sexually crossing one plant with another plant, such as, cross-pollinating, may be accomplished or facilitated by human intervention, for example: by human hands collecting the pollen of one plant and contacting this pollen with the style or stigma of a second plant; by human hands and/or human actions removing, destroying, or covering the stamen or anthers of a plant (for example, by manual intervention or by application of a chemical gametocide) so that natural self-pollination is prevented and cross-pollination would have to take place in order for fertilization to occur; by human placement of pollinating insects in a position for "directed pollination" (for example, by placing beehives in orchards or fields or by caging plants with pollinating insects); by human opening or removing of parts of the flower to allow for placement or contact of foreign pollen on the style or stigma; by selective placement of plants (for example, intentionally planting plants in pollinating proximity); and/or by application of chemicals to precipitate flowering or to foster receptivity (of the stigma for pollen).

In practicing this method, the step of sexually crossing one plant with itself, such as, self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (for example, by detasseling or by application of a chemical gametocide) so that natural cross-pollination is prevented and self-pollination would have to take place in order for fertilization to occur; by human placement of pollinating insects in a position for "directed pollination" (for example, by caging a plant alone with pollinating insects); by human manipulation of the flower or its parts to allow for self-pollination; by selective placement of plants (for example, intentionally planting plants beyond pollinating proximity); and/or by application of chemicals to precipitate flowering or to foster receptivity (of the stigma for pollen).

The present invention provides a plant part that is derived from a plant comprising event KK179-2. As used herein, a "plant part" refers to any part of a plant that is comprised of material derived from a plant comprising event KK179-2. Plant parts include but are not limited to pollen, ovule, pod, flower, root or stem tissue, fibers, and leaf. Plant parts may be viable, nonviable, regenerable, and/or non-regenerable.

The present invention provides a commodity product that is derived from a plant comprising event KK179-2. As used herein, a "commodity product" refers to any composition or product that is comprised of material derived from a plant, seed, plant cell, or plant part comprising event KK179-2. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, and any other food for human consumption; and biomasses and fuel products. Processed alfalfas are the largest source of forage legume in the world. A plant comprising event KK179-2 can thus be used to manufacture any commodity product typically acquired from an alfalfa plant. Any such commodity product that is derived from the plants comprising event KK179-2 may contain at least a detectable amount of the specific and unique DNA corresponding to event KK179-2, and specifically may contain a detectable amount of a polynucleotide having a nucleotide sequence of the consecutive nucleotides of SEQ ID NO: 1 and the consecutive nucleotides of SEQ ID NO: 2. Any standard method of detection for polynucleotide molecules may be used, including methods of detection disclosed herein. A commodity product is within the scope of the present invention if there is any detectable amount of the consecutive nucleotides of SEQ ID NO: 1 or the consecutive nucleotides of SEQ ID NO: 2, in the commodity product.

The plant, progeny, seed, plant cell, plant part (such as pollen, ovule, pod, flower, root or stem tissue, and leaf), and commodity products of the present invention are therefore useful for, among other things, growing plants for the purpose of producing seed and/or plant parts comprising event KK179-2 for agricultural purposes, producing progeny comprising event KK179-2 for plant breeding and research purposes, use with microbiological techniques for industrial and research applications, and sale to consumers.

The present invention provides methods for producing plants with reduced lignin and plants comprising event KK179-2. Event KK179-2 plant was produced by an *Agrobacterium* mediated transformation method similar to that described in U.S. Pat. No. 5,914,451, using an inbred alfalfa line with the construct pFG118. Construct pFG118 contains a plant suppression cassette for downregulation of the CCOMT enzyme in alfalfa plant cells. Transgenic alfalfa cells were regenerated into intact alfalfa plants and individual plants were selected from the population of independently transformed transgenic plants that showed desirable molecular characteristics, such as, the integrity of the transgene cassette, absence of the construct backbone sequence, loss of the unlinked kanamycin resistance selection cassette. Furthermore, inverse PCR and DNA sequence analyses were performed to determine the 5' and 3' insert-to-plant genome junctions, to confirm the organization of the elements within the insert (FIG. 1), and to determine the complete DNA sequence of the insert in alfalfa event KK179-2 (SEQ ID NO: 5). In addition, transgenic plants were screened and selected for reduced lignin under field conditions. An alfalfa plant that contains in its genome the suppression cassette of pFG118 is an aspect of the present invention.

Methods for producing a plant with reduced lignin comprising transgenic event KK179-2 are provided. Transgenic plants used in these methods may be heterozygous for the transgene. Progeny plants produced by these methods may be varietal or hybrid plants; may be grown from seeds produced by a plant and/or from seed comprising event KK179-2 produced by a plant fertilized with pollen from a plant comprising event KK179-2; and may be homozygous or heterozygous for the transgene. Progeny plants may be subsequently self-pollinated to generate a true breeding line of plants, such as, plants homozygous for the transgene, or alternatively may be outcrossed, for example, bred with another unrelated plant, to produce a varietal or a hybrid seed or plant. As used herein, the term "zygosity" refers to the similarity of DNA at a specific chromosomal location (locus) in a plant. In the present invention, the DNA specifically refers to the transgene insert along with the junction sequence (event DNA). A plant is homozygous if the transgene insert with the junction sequence is present at the same location on each chromosome of a chromosome pair (4 alleles). A plant is considered heterozygous if the transgene insert with the junction sequence is present on only one chromosome of a chromosome pair (1 allele). A wild-type plant is null for the event DNA.

Progeny plants and seeds encompassed by these methods and produced by using these methods are distinct from other plants, for example, because the progeny plants and seeds are recombinant and as such created by human intervention; contain at least one allele that consists of the transgenic DNA of the present invention; and/or contain a detectable amount of a polynucleotide sequence selected from the group consisting of consecutive nucleotides of SEQ ID NO: 1, or consecutive nucleotides of SEQ ID NO: 2. A seed may be selected from an individual progeny plant, and so long as the seed comprises SEQ ID NO: 1, or SEQ ID NO: 2, it will be within the scope of the present invention.

The plants, progeny, seeds, plant cells, plant parts (such as pollen, ovule, pod, flower, root or stem tissue, and leaves), and commodity products of the present invention may be evaluated for DNA composition, gene expression, and/or protein expression. Such evaluation may be done by using various methods such as PCR, sequencing, northern blotting, southern analysis, western blotting, immuno-precipitation, and ELISA or by using the methods of detection and/or the detection kits provided herein.

Methods of detecting the presence of compositions specific to event KK179-2 in a sample are provided. One method consists of detecting the presence of DNA specific to and derived from a cell, a tissue, a seed, a plant or plant parts comprising event KK179-2. The method provides for a template DNA sample to be contacted with a primer pair that is capable of producing an amplicon from event KK179-2 DNA upon being subjected to conditions appropriate for amplification, particularly an amplicon that comprises SEQ ID NO: 1, and/or SEQ ID NO: 2, or the complements thereof. The amplicon is produced from a template DNA molecule derived from event KK179-2, so long as the template DNA molecule incorporates the specific and unique nucleotide sequences of SEQ ID NO: 1, or SEQ ID NO: 2. The amplicon may be single or double stranded DNA or RNA, depending on the polymerase selected for use in the production of the amplicon. The method provides for detecting the amplicon molecule produced in any such amplification reaction, and confirming within the sequence of the amplicon the presence of the nucleotides corresponding to SEQ ID NO: 1, or SEQ ID NO: 2, or the complements thereof. The detection of the nucleotides corresponding to SEQ ID NO: 1, and/or SEQ ID NO: 2, or the complements thereof in the amplicon are determinative and/or diagnostic for the presence of event KK179-2 specific DNA and thus biological material comprising event KK179-2 in the sample.

Another method is provided for detecting the presence of a DNA molecule corresponding to SEQ ID NO: 3 or SEQ ID NO: 4 in a sample consisting of material derived from plant or plant tissue. The method consists of (i) obtaining a DNA sample from a plant, or from a group of different plants, (ii) contacting the DNA sample with a DNA probe molecule comprising the nucleotides as set forth in either SEQ ID NO: 1 or SEQ ID NO: 2, (iii) allowing the probe and the DNA sample to hybridize under stringent hybridization conditions, and then (iv) detecting a hybridization event between the probe and the target DNA sample. Detection of the hybrid composition is diagnostic for the presence of SEQ ID NO: 3 or SEQ ID NO: 4, as the case may be, in the DNA sample. Absence of hybridization is alternatively diagnostic of the absence of the transgenic event in the sample if the appropriate positive controls are run concurrently. Alternatively, determining that a particular plant contains either or both of the sequences corresponding to SEQ ID NO: 1 or SEQ ID NO: 2, or the complements thereof, is determinative that the plant contains at least one allele corresponding to event KK179-2.

It is thus possible to detect the presence of a nucleic acid molecule of the present invention by any well known nucleic acid amplification and detection methods such as polymerase chain reaction (PCR), recombinase polymerase amplification (RPA), or DNA hybridization using nucleic acid probes. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for transgenic event RT73 is demonstrated. In this study, event-specific primers and probes were designed based upon the sequences of the genome/transgene junctions for each event. Transgenic plant event specific DNA detection methods have also been described in U.S. Pat. Nos. 7,632,985; 7,566,817; 7,368,241; 7,306,909; 7,718,373; 7,189,514, 7,807,357 and 7,820,392.

DNA detection kits are provided. One type of kit contains at least one DNA molecule of sufficient length of contiguous nucleotides of SEQ ID NO: 3, SEQ ID NO: 5, or SEQ ID NO: 6 to function as a DNA primer or probe specific for detecting the presence of DNA derived from transgenic event KK179-2 in a sample. The DNA molecule being detected with the kit comprises contiguous nucleotides of the sequence as set forth in SEQ ID NO: 1. Alternatively, the kit may contain at least one DNA molecule of sufficient length of contiguous nucleotides of SEQ ID NO: 4, SEQ ID NO: 5, or SEQ ID NO: 6 to function as a DNA primer or probe specific for detecting the presence of DNA derived from transgenic event KK179-2 in a sample. The DNA molecule being detected with the kit comprises contiguous nucleotides as set forth in SEQ ID NO: 2.

An alternative kit employs a method in which the target DNA sample is contacted with a primer pair as described above, then performing a nucleic acid amplification reaction sufficient to produce an amplicon comprising the consecutive nucleotides of SEQ ID NO: 1, and SEQ ID NO: 2. Detection of the amplicon and determining the presence of the consecutive nucleotides of SEQ ID NO: 1, and SEQ ID NO: 2 or the complements thereof within the sequence of the amplicon is diagnostic for the presence of event KK179-2 specific DNA in a DNA sample.

A DNA molecule sufficient for use as a DNA probe is provided that is useful for determining, detecting, or for diagnosing the presence or even the absence of DNA specific and unique to event KK179-2 DNA in a sample. The DNA molecule contains the consecutive nucleotides of SEQ ID NO: 1, or the complement thereof, and the consecutive nucleotides of SEQ ID NO: 2, or the complement thereof.

Nucleic acid amplification can be accomplished by any of the various nucleic acid amplification methods known in the art, including thermal and isothermal amplification methods. The sequence of the heterologous DNA insert, junction sequences, or flanking sequences from event KK179-2 (with representative seed samples comprising event KK179-2 deposited as ATCC PTA-11883) can be verified by amplifying such sequences from the event using primers derived from the sequences provided herein followed by standard DNA sequencing of the amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed which overlaps both the adjacent flanking genomic DNA sequence and the inserted DNA sequence. The oligonucleotide is immobilized in wells of a microwell plate. Following thermal amplification of the region of interest (using one primer in the inserted sequence and one in the adjacent flanking genomic sequence), a single-stranded amplicon can be hybridized to the immobilized oligonucleotide and serve as a template for a single base extension reaction using a DNA polymerase and labelled ddNTPs specific for the expected next base. Readout may be fluorescent or ELISA-based. Detection of a fluorescent or other signal indicates the presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to a single-stranded amplicon from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. ddNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon. Using this method an oligonucleotide is designed which overlaps the genomic flanking and inserted DNA junction. The oligonucleotide is hybridized to single-stranded amplicon from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) may also be used to detect and/or quantifying the presence of a DNA sequence using the instructions provided by the manufacturer. Briefly, a FRET oligonucleotide probe is designed which overlaps the genomic flanking and insert DNA junction. The FRET probe and amplification primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and amplification primers (one primer in the insert DNA sequence and one in the flanking genomic sequence) are cycled in the presence of a thermostable polymerase and dNTPs. Following successful amplification, hybridization of the FRET probe to the target sequence results in the removal of the probe secondary structure and spatial separation of the fluorescent and quenching moieties resulting in the production of a fluorescent signal. The fluorescent signal indicates the presence of the flanking/transgene insert sequence due to successful amplification and hybridization.

Other described methods, such as, microfluidics (US Patent Publication No. 2006068398, U.S. Pat. No. 6,544,734) provide methods and devices to separate and amplify DNA samples. Optical dyes are used to detect and measure specific DNA molecules (WO/05017181). Nanotube devices (WO/06024023) that comprise an electronic sensor for the detection of DNA molecules or nanobeads that bind specific DNA molecules and can then be detected.

DNA detection kits can be developed using the compositions disclosed herein and the methods well known in the art of DNA detection. The kits are useful for the identification of event KK179-2 in a sample and can be applied to methods for breeding plants containing the appropriate event DNA. The kits may contain DNA primers or probes that are similar or complementary to SEQ ID NO: 1-6, or fragments or complements thereof.

The kits and detection methods of the present invention are therefore useful for, among other things, identifying event KK179-2, selecting plant varieties or hybrids comprising event KK179-2, detecting the presence of DNA derived from event KK179-2 in a sample, and monitoring samples for the presence and/or absence of event KK179-2 or plants, plant parts or commodity products comprising event KK179-2.

The following examples are included to demonstrate examples of certain embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1: Isolation of Flanking Sequences Using Inverse PCR and Identification of Flanking Sequences by Sequencing This example describes isolation of the alfalfa genomic DNA sequences flanking the transgenic DNA insert using inverse PCR for event KK179-2, and identification of the flanking genomic sequences by sequencing.

Sequences flanking the T-DNA insertion in event KK179-2 were determined using inverse PCR as described in Ochman et al., 1990 (PCR Protocols: A guide to Methods and Applications, Academic Press, Inc.). Plant genomic DNA was isolated from both wild-type R2336 and the transgenic line from tissue grown under greenhouse conditions. Frozen leaf tissue was ground with a mortar and a pestle in liquid nitrogen or by mechanical grinding, followed by DNA extraction using methods known in the art. This method can be modified by one skilled in the art to extract DNA from any tissue, including, but not limited to seed.

An aliquot of DNA from each sample was digested with restriction endonucleases selected based on restriction analysis of the transgenic DNA. After self-ligation of the restriction fragments, PCR amplification was performed using primers designed from the transgenic sequence that would amplify sequences extending away from the 5' and 3' ends of the transgenic DNA. A variety of Taq polymerases and amplification systems may be used. Table 2 shows an example of PCR amplification for flanking sequence isolation using Phusion High Fidelity DNA Polymerase (Cat. No. F531S or F531L, New England Biolabs), and Thermalcyclers Applied Biosystems GeneAmp 9700, ABI 9800 Fast Thermal Cycler and MJ Opticon.

TABLE 1

An example of inverse PCR amplification for flanking sequence isolation.

| | Volume | Component |
|---|---|---|
| PCR master mix (per reaction) | 2.9 µl | water |
| | 0.05 µl | Primer 1 (100 µM) |
| | 0.05 µl | Primer 1 (100 µM) |
| | 5.0 µl | 2X Phusion Taq |
| | 2.0 µl | ligated DNA |
| | 10 µl | Total |

| | Step | Condition |
|---|---|---|
| DNA amplification in a fast thermocycler | 1 | 98° C. 30 sec |
| | 2 | 98° C. 5 sec |
| | 3 | 60° C. 10 sec |
| | 4 | 72° C. 2 min |
| | 5 | Go to step 2 30 times |
| | 6 | 72° C. 4 min |
| | 7 | 10° C. forever |
| | 8 | End |

PCR products were separated by agarose gel electrophoresis and purified using a QIAGEN gel purification kit (Qiagen, Valencia, Calif.). The subsequent products were sequenced directly using standard sequencing protocols. Using these two methods, the 5' flanking sequence, which extends into the left border sequence of the integrated DNA insert including the CCOMT suppression cassette, was identified and is presented as SEQ ID NO: 3 ([C] of FIG. 1). The 3' flanking sequence, which extends into the right border sequence of the integrated DNA insert including the CCOMT suppression cassette, was identified and is presented as SEQ ID NO: 4 ([D] of FIG. 1). The transgenic DNA integrated into the R2336 genomic DNA is presented as SEQ ID NO: 5 ([E] of FIG. 1).

The isolated sequences were compared to the T-DNA sequence to identify the flanking sequences and the co-isolated T-DNA fragments. Confirmation of the presence of the expression cassette was achieved by PCR with primers designed based upon the deduced flanking sequence data and the known T-DNA sequence. The R2336 wild type sequence corresponding to the same region in which the T-DNA was integrated in the transformed line was isolated using primers designed from the flanking sequences in KK179-2. The flanking sequences in KK179-2 and the R2336 wild type sequence were analyzed against multiple nucleotide and protein databases. This information was used to examine the relationship of the transgene to the plant genome and to look at the insertion site integrity. The flanking sequence and wild type sequences were used to design primers for TAQMAN® endpoint assays used to identify the events as described in Example 2

Example 2: Event-Specific Endpoint TAQMAN®

This example describes an event-specific endpoint TAQMAN® thermal amplification method for identification of event KK179-2 DNA in a sample.

Examples of conditions useful with the event KK179-2-specific endpoint TAQMAN® method are described in Table 2 and Table 3. The DNA primers used in the endpoint assay are primers SQ20901 (SEQ ID NO: 7) and SQ23728 (SEQ ID NO: 8) and 6-FAM™ labeled oligonucleotide probe PB10164 (SEQ ID NO: 9). 6FAM™ is a fluorescent dye product of Applied Biosystems (Foster City, Calif.) attached to the DNA probe. For TAQMAN® MGB (Minor Groove Binding) probes, the 5'exonuclease activity of Taq DNA polymerase cleaves the probe from the 5'-end, between the fluorophore and quencher. When hybridized to the target DNA strand, quencher and fluorophore are separated enough to produce a fluorescent signal.

Primers SQ20901 (SEQ ID NO: 7) and SQ23728 (SEQ ID NO: 8) when used as described with probe PB10164 (SEQ ID NO: 9) produce an amplicon of 81 nt that is diagnostic for event KK179-2 DNA. The analysis includes a positive control from alfalfa known to contain event KK179-2 DNA, a negative control from non-transgenic alfalfa and a negative control that contains no template DNA.

These assays are optimized for use with Applied Biosystems GeneAmp PCR System 9700, ABI 9800 Fast Thermal Cycler and MJ Research DNA Engine PTC-225. Other methods and apparatus known to those skilled in the art may be used to produce amplicons that identify the event KK179-2 DNA.

TABLE 2

Alfalfa KK179-2 Event-Specific Endpoint TAQMAN ® PCR Conditions

| Step | Reagent | Volume | Comments |
|---|---|---|---|
| 1 | 18 megohm water | adjust for final volume of 10 µl | |
| 2 | 2X Universal Master Mix (dNTPs, enzyme and buffer) | 5.0 µl | 1X final concentration of dNTPs, enzyme and buffer |
| 3 | Event Primers SQ20901 and SQ23728 Mix (resuspended in 18 megohm water to a concentration of 20 µM for each primer) Example: In a microcentrifuge tube, the following are added to achieve 500 µl at a final concentration of 20 µM: 100 µl of Primer SQ20901 at a concentration of 100 µM 100 µl of Primer SQ23728 at a concentration of 100 µM 300 µl of 18 megohm water | 0.5 µl | 1.0 µM final concentration |
| 4 | Event 6-FAM ™ MGB Probe PB10164 (resuspended in 18 megohm water to a concentration of 10 µM) | 0.2 µl | 0.2 µM final concentration |

TABLE 2-continued

Alfalfa KK179-2 Event-Specific Endpoint TAQMAN® PCR Conditions

| Step | Reagent | Volume | Comments |
|---|---|---|---|
| 5 | Internal control Primer-1 and internal control Primer-2 Mix (resuspended in 18 megohm water to a concentration of 20 µM for each primer) | 0.5 µl | 1 µM final concentration |
| 6 | Internal control VIC ™ probe (resuspended in 18 megohm water to a concentration of 10 µM) | 0.2 µl | 0.2 µM final concentration |
| 7 | Extracted DNA (template): 1. Leaf or seed samples to be analyzed 2. Negative control (non-transgenic DNA) 3. Negative water control (no template control) 4. Positive control (KK179-2 DNA) | 3.0 µl | |

TABLE 3

Endpoint TAQMAN® thermocycler conditions

| Cycle No. | | Settings |
|---|---|---|
| 1 | 50° C. | 2 minutes |
| 1 | 95° C. | 10 minutes |
| 10 | 95° C. | 15 seconds |
|  | 64° C. | 1 minute (−1° C./cycle) |
| 30 | 95° C. | 15 seconds |
|  | 54° C. | 1 minute |
| 1 | 10° C. | Forever |

A deposit of representative alfalfa event KK179-2 seed disclosed above and recited in the claims, has been made under the Budapest Treaty with the American Type Culture Collection (ATCC), 10801 University Boulevard, Manassas, Va. 20110. The ATCC accession number is PTA-11833. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

Example 3

Example 3: ADL Measurements in the Lower Stem of Reduced Lignin Alfalfa Events

TABLE 4

Lower stem ADL measurements for the 6 reduced lignin alfalfa events in two fall dormant (FD) germplasms from 3 locations in 2008

| Event | Dormancy germplasm | Event Mean | Delta | Delta LCI @ 90% | Delta UCI @ 90% | % Diff. | P-value |
|---|---|---|---|---|---|---|---|
| JJ041 | FD | 7.91 | −1.75 | −1.97 | −1.52 | −18.09 | <.001 |
| JJ266 | FD | 7.48 | −2.18 | −2.39 | −1.98 | −22.60 | <.001 |
| KK136 | FD | 7.01 | −2.64 | −2.90 | −2.39 | −27.40 | <.001 |
| KK179 | FD | 7.65 | −2.01 | −2.24 | −1.79 | −20.83 | <.001 |
| KK376 | FD | 7.37 | −2.29 | −2.55 | −2.04 | −23.75 | <.001 |
| KK465 | FD | 7.30 | −2.36 | −2.59 | −2.13 | −24.44 | <.001 |
| JJ041 | FD | 7.71 | −1.77 | −2.01 | −1.53 | −18.70 | <.001 |
| JJ266 | FD | 6.98 | −2.50 | −2.74 | −2.26 | −26.38 | <.001 |
| KK136 | FD | 7.38 | −2.10 | −2.34 | −1.86 | −22.14 | <.001 |
| KK179 | FD | 7.56 | −1.92 | −2.16 | −1.68 | −20.24 | <.001 |
| KK376 | FD | 6.51 | −2.97 | −3.21 | −2.73 | −31.33 | <.001 |
| KK465 | FD | 7.33 | −2.15 | −2.39 | −1.91 | −22.68 | <.001 |

Abbreviations used in the tables that follow:
ADL = Acid Detergent Lignin, % of dry matter
LSD = Least Significant Difference
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Event positive plants in Table 4 showed a significant ($p \leq 0.05$) decrease in lower stem ADL which ranged from 18-31% when compared to the pooled negative control. KK179-2 alfalfa event has the reduced lignin phenotype identified by the "sweet spot" selection method.

TABLE 5

Lower stem ADL measurements for the 6 reduced lignin alfalfa lead events in fall dormant (FD) germplasms grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 9.46 | 10.79 | −1.32 | −1.55 | −1.09 | −12.26 | <.001 |
| JJ266 | 8.53 | 10.79 | −2.26 | −2.47 | −2.05 | −20.95 | <.001 |
| KK136 | 8.52 | 10.79 | −2.27 | −2.53 | −2.02 | −21.06 | <.001 |
| KK179 | 8.52 | 10.79 | −1.96 | −2.53 | −1.74 | −18.20 | <.001 |
| KK376 | 8.49 | 10.79 | −2.29 | −2.54 | −2.04 | −21.26 | <.001 |
| KK465 | 8.55 | 10.79 | −2.24 | −2.47 | −2.00 | −20.73 | <.001 |

Abbreviations used in the tables that follow:
ADL = Acid Detergent Lignin, % of dry matter
LSD = Least Significant Difference
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 6

Lower stem ADL measurements for the 6 reduced lignin alfalfa lead events in fall dormant (FD) germplasms grown at 2 locations in 2009

| Event | Event Mean | Control Mean | Delta | Delta LCI @ 90% | Delta UCI @ 90% | % Diff. | P-value |
|---|---|---|---|---|---|---|---|
| JJ041 | 9.42 | 11.73 | −2.31 | −2.61 | −2.02 | −19.72 | <.001 |
| JJ266 | 8.84 | 11.73 | −2.89 | −3.18 | −2.59 | −24.61 | <.001 |
| KK136 | 9.27 | 11.73 | −2.46 | −2.79 | −2.12 | −20.94 | <.001 |
| KK179 | 9.45 | 11.73 | −1.28 | −2.57 | −1.98 | −19.41 | <.001 |

TABLE 6-continued

Lower stem ADL measurements for
the 6 reduced lignin alfalfa lead events in fall
dormant (FD) germplasms grown at 2 locations in 2009

| Event | Event Mean | Control Mean | Delta | Delta LCI @ 90% | Delta UCI @ 90% | % Diff. | P-value |
|---|---|---|---|---|---|---|---|
| KK376 | 8.73 | 11.73 | −3.00 | −3.30 | −2.70 | −25.57 | <.001 |
| KK465 | 9.17 | 11.73 | −2.56 | −2.85 | −2.27 | −21.84 | <.001 |

Abbreviations used in the tables that follow:
ADL = Acid Detergent Lignin, % of dry matter
LSD = Least Significant Difference
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 7

Lower stem ADL measurements for
the 6 reduced lignin alfalfa lead events in non
dormant (ND) germplasms grown at 4 locations in 2009

| Event | Event Mean | Control Mean | Delta | Delta LCI @ 90% | Delta UCI @ 90% | % Diff. | P-value |
|---|---|---|---|---|---|---|---|
| JJ041 | 9.31 | 10.89 | −1.58 | −1.81 | −1.35 | −14.50 | <.001 |
| JJ266 | 8.11 | 10.89 | −2.79 | −3.01 | −2.56 | −25.58 | <.001 |
| KK136 | 8.55 | 10.89 | −2.34 | −2.57 | −2.11 | −21.50 | <.001 |
| KK179 | 8.87 | 10.89 | −2.03 | −2.26 | −1.80 | −18.61 | <.001 |
| KK376 | 8.26 | 10.89 | −2.63 | −2.86 | −2.40 | −24.14 | <.001 |
| KK465 | 9.09 | 10.89 | −1.81 | −2.03 | −1.58 | −16.58 | <.001 |

Abbreviations used in the tables that follow:
ADL = Acid Detergent Lignin, % of dry matter
LSD = Least Significant Difference
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 8

Lower stem ADL measurements for
6 reduced lignin alfalfa lead events in non
dormant (ND) germplasms grown at 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 8.91 | 11.16 | −2.26 | −2.64 | −1.87 | −20.21 | <.001 |
| JJ266 | 8.53 | 11.16 | −2.63 | −3.02 | −2.25 | −23.61 | <.001 |
| KK136 | 8.85 | 11.16 | −2.31 | −2.69 | −1.92 | −20.67 | <.001 |
| KK179 | 8.75 | 11.16 | −2.41 | −2.80 | −2.02 | −21.58 | <.001 |
| KK376 | 8.35 | 11.16 | −2.81 | −3.20 | −2.42 | −25.16 | <.001 |
| KK465 | 9.14 | 11.16 | −2.03 | −2.41 | −1.64 | −18.15 | <.001 |

Abbreviations used in the tables that follow:
ADL = Acid Detergent Lignin, % of dry matter
LSD = Least Significant Difference
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Tables 6-8 show 2009 data for lower stem ADL in a fall dormant (FD) and non dormant (ND) germplasms at 4 and 2 locations respectively. The 6 event positive lines showed a significant (p≤0.05) reduction in ADL ranging from 12-26% when compared to the pooled negative control, with the lead event KK179 showing a reduction in ADL of 18-22%.

Example 4

Example 4: NDFD Measurements in the Lower Stem of Reduced Lignin Alfalfa Events

TABLE 9

Lower stem NDFD measurements for
the 6 reduced lignin alfalfa lead events in fall
dormant (FD) germplasms grown at 3 locations in 2008

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | FD | 32.68 | 27.70 | 4.98 | 4.23 | 5.73 | 17.98 | <.001 |
| JJ266 | FD | 33.58 | 27.70 | 5.88 | 5.20 | 6.56 | 21.23 | <.001 |
| KK136 | FD | 35.46 | 27.70 | 7.76 | 6.91 | 8.61 | 28.01 | <.001 |
| KK179 | FD | 33.52 | 27.70 | 5.82 | 5.08 | 6.57 | 21.02 | <.001 |
| KK376 | FD | 34.12 | 27.70 | 6.43 | 5.57 | 7.28 | 23.20 | <.001 |
| KK465 | FD | 35.33 | 27.70 | 7.63 | 6.88 | 8.38 | 27.55 | <.001 |
| JJ041 | FD | 33.27 | 27.70 | 5.56 | 4.69 | 6.44 | 20.08 | <.001 |
| JJ266 | FD | 34.98 | 27.70 | 7.27 | 6.40 | 8.15 | 26.25 | <.001 |
| KK136 | FD | 34.29 | 27.70 | 6.59 | 5.71 | 7.46 | 23.77 | <.001 |
| KK179 | FD | 33.13 | 27.70 | 5.42 | 4.54 | 6.30 | 19.57 | <.001 |
| KK376 | FD | 37.44 | 27.70 | 9.74 | 8.86 | 10.61 | 35.14 | <.001 |
| KK465 | FD | 35.34 | 27.70 | 7.64 | 6.76 | 8.52 | 27.57 | <.001 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Lower stem NDFD for the 6 reduce lignin events in fall dormant (FD) germplasms at 3 locations. Event positive plants showed a significant (p≤0.05) increase in lower stem NDFD which ranged from 18-35% when compared to the pooled negative control.

TABLE 10

Lower stem NDFD measurements for
the 6 reduced lignin alfalfa lead events in fall
dormant (FD) germplasms grown at 4 locations in 2009

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | FD | 28.09 | 22.31 | 5.79 | 4.89 | 6.69 | 25.95 | <.001 |
| JJ266 | FD | 28.58 | 22.31 | 6.27 | 5.46 | 7.08 | 28.11 | <.001 |
| KK136 | FD | 28.88 | 22.31 | 6.57 | 5.58 | 7.56 | 29.46 | <.001 |
| KK179 | FD | 27.20 | 22.31 | 4.90 | 4.01 | 5.78 | 21.95 | <.001 |
| KK376 | FD | 28.65 | 22.31 | 6.34 | 5.38 | 7.31 | 28.43 | <.001 |
| KK465 | FD | 28.21 | 22.31 | 5.91 | 4.99 | 6.83 | 26.49 | <.001 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 11

Lower stem NDFD measurements for the 6 reduced lignin alfalfa lead events in non dormant (ND) germplasms grown at 2 locations in 2009

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | ND | 26.84 | 20.88 | 5.96 | 4.62 | 7.30 | 28.52 | <.001 |
| JJ266 | ND | 27.79 | 20.88 | 6.90 | 5.63 | 8.18 | 33.06 | <.001 |
| KK136 | ND | 27.47 | 20.88 | 6.59 | 5.14 | 8.05 | 31.56 | <.001 |
| KK179 | ND | 26.73 | 20.88 | 5.85 | 4.51 | 7.18 | 27.99 | <.001 |
| KK376 | ND | 27.19 | 20.88 | 6.31 | 4.97 | 7.65 | 30.21 | <.001 |
| KK465 | ND | 27.02 | 20.88 | 6.14 | 4.86 | 7.42 | 29.41 | <.001 |

Abbreviations used in the tables that follow:

NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))

ND = Non Dormant

KK179 = KK179-2 reduced lignin alfalfa lead event

Delta = difference between Event and Control means (Event − Control)

% Diff = Percent difference between Event and Control (Delta/Control * 100)

Delta LCI @ 90% = Lower Confidence Interval of Delta value using an alpha level of 0.10

Delta UCI @ 90% = Upper Confidence Interval of Delta value using an alpha level of 0.10

P-value = probability of a greater absolute difference under the null hypothesis (2-tailed test for significance).

TABLE 12

Lower stem NDFD measurements for the 6 reduced lignin alfalfa lead events in fall dormant (FD) germplasms grown at 4 locations in 2009

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | FD | 27.96 | 22.11 | 5.85 | 5.01 | 6.69 | 26.46 | <.001 |
| JJ266 | FD | 29.97 | 22.11 | 7.86 | 7.01 | 8.70 | 35.54 | <.001 |
| KK136 | FD | 28.84 | 22.11 | 6.73 | 5.89 | 7.58 | 30.45 | <.001 |
| KK179 | FD | 27.32 | 22.11 | 5.21 | 4.37 | 6.06 | 23.58 | <.001 |
| KK376 | ND | 29.81 | 22.11 | 7.70 | 6.85 | 8.54 | 34.82 | <.001 |
| KK465 | ND | 27.37 | 22.11 | 5.26 | 4.41 | 6.10 | 23.78 | <.001 |

Abbreviations used in the tables that follow:

NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))

FD = Fall Dormant

ND = Non Dormant

KK179 = KK179-2 reduced lignin alfalfa lead event

Delta = difference between Event and Control means (Event − Control)

% Diff = Percent difference between Event and Control (Delta/Control * 100)

Delta LCI @ 90% = Lower Confidence Interval of Delta value using an alpha level of 0.10

Delta UCI @ 90% = Upper Confidence Interval of Delta value using an alpha level of 0.10

P-value = probability of a greater absolute difference under the null hypothesis (2-tailed test for significance).

TABLE 13

Lower stem NDFD measurements for the 6 reduced lignin alfalfa lead events in non dormant (ND) germplasms grown at 2 locations in 2009

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | ND | 28.10 | 22.39 | 5.71 | 4.15 | 7.26 | 25.48 | <.001 |
| JJ266 | ND | 28.73 | 22.39 | 6.34 | 4.78 | 7.89 | 28.29 | <.001 |
| KK136 | ND | 28.66 | 22.39 | 6.27 | 4.71 | 7.82 | 28.00 | <.001 |
| KK179 | ND | 27.76 | 22.39 | 5.37 | 3.81 | 6.92 | 23.98 | <.001 |
| KK376 | ND | 29.87 | 22.39 | 7.48 | 5.93 | 9.04 | 33.40 | <.001 |
| KK465 | ND | 28.95 | 22.39 | 56.56 | 5.00 | 8.11 | 29.29 | <.001 |

Abbreviations used in the tables that follow:

NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))

ND = Non Dormant

KK179 = KK179-2 reduced lignin alfalfa lead event

Delta = difference between Event and Control means (Event − Control)

% Diff = Percent difference between Event and Control (Delta/Control * 100)

Delta LCI @ 90% = Lower Confidence Interval of Delta value using an alpha level of 0.10

Delta UCI @ 90% = Upper Confidence Interval of Delta value using an alpha level of 0.10

P-value = probability of a greater absolute difference under the null hypothesis (2-tailed test for significance).

Table 11-13 show 2009 data for lower stem NDFD in fall dormant (FD) and non dormant (ND) germplasm at 4 and 2 locations respectively. The 6 event positive reduced lignin alalfa events showed a significant (p≤0.05) increase in NDFD ranging from 22-36% when compared to the pooled negative control, with the lead event KK179-2 showing an increase in NDFD of 22-28%.

Example 5
Example 5: Vigor Rating for Reduced Lignin Alfalfa Events

TABLE 14

Vigor ratings for the 2 reduced lignin alfalfa events, JJ266 and KK179-2 compared to commercial checks and the null controls in 3 locations. The reduced lignin event KK179-2 resulted in no off-types for vigor rating scale.

| Event | Location 1 | Location 2 | Location 3 | Mean |
|---|---|---|---|---|
| JJ266 | 8.0 | 7.4 | 7.8 | 7.7 |
| JJ266, null | 7.8 | 7.4 | 8.0 | 7.7 |
| KK179-2 | 8.0 | 7.6 | 7.6 | 7.7 |
| KK179, null | 7.4 | 7.7 | 8.1 | 7.7 |
| Commercial Check 1 | 6.9 | 6.7 | 7.1 | 6.9 |
| Commercial Check 2 | 7.1 | 7.0 | 6.7 | 6.9 |
| Commercial Check 3 | 7.8 | 8.1 | 8.1 | 8.0 |
| Commercial Check 4 | 7.3 | 7.6 | 7.9 | 7.6 |

Data collected for these trials are as follows: plant vigor (scored 1-10, 10 being best) taken 21 days after previous harvest and the second week of May for the spring score, lodging tolerance (scored 1-10, 10 being perfectly upright) taken 1-5 days prior to harvest per season. Plant yield (grams of dry matter (DM) per plant) taken after plants were dried, NDFD (using CAI NIR calibration for RL alfalfa) and ADL (using NIR calibration for RL alfalfa).

Example 6
Example 6: ADL Measurements in the Whole Plant for Reduced Lignin Alfalfa Events

TABLE 15

Whole plant hay ADL measurements for the 6 reduced lignin alfalfa lead events in fall dormant (FD) germplasms grown in 4 locations in 2009

| Event | Event Mean | Control Mean | Delta | Delta LCI @ 90% | Delta UCI @ 90% | % Diff. | P-value |
|---|---|---|---|---|---|---|---|
| JJ041 | 4.96 | 5.66 | −0.69 | −1.55 | −0.44 | −12.27 | <.001 |
| JJ266 | 4.85 | 5.66 | −1.04 | −2.47 | −0.59 | −14.37 | <.001 |
| KK136 | 4.81 | 5.66 | −1.12 | −2.53 | −0.59 | −15.09 | <.001 |
| KK179 | 5.11 | 5.66 | −0.80 | −2.19 | −0.31 | −9.79 | <.001 |
| KK376 | 4.73 | 5.66 | −1.19 | −2.54 | −0.66 | −16.39 | <.001 |
| KK465 | 5.18 | 5.66 | −0.74 | −2.47 | −0.22 | −8.49 | 0.002 |

Abbreviations used in the tables that follow:
ADL = Acid Detergent Lignin, % of dry matter
LSD = Least Significant Difference
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 16

Whole plant hay ADL measurements for the 6 reduced lignin alfalfa lead events in non dormant (ND) germplasms grown in 2 locations in 2009

| Event | Event Mean | Control Mean | Delta | Delta LCI @ 90% | Delta UCI @ 90% | % Diff. | P-value |
|---|---|---|---|---|---|---|---|
| JJ041 | 5.40 | 6.16 | −0.77 | −1.22 | −0.31 | −12.43 | 0.006 |
| JJ266 | 5.27 | 6.16 | −0.89 | −1.30 | −0.48 | −14.47 | 0.000 |
| KK136 | 5.56 | 6.16 | −0.61 | −1.07 | −0.15 | −9.87 | 0.030 |
| KK179 | 5.41 | 6.16 | −0.76 | −1.19 | −0.32 | −12.25 | 0.004 |
| KK376 | 5.20 | 6.16 | −0.97 | −1.42 | −0.51 | −15.66 | 0.001 |
| KK465 | 5.57 | 6.16 | −0.60 | −1.00 | −0.19 | −9.69 | 0.016 |

Abbreviations used in the tables that follow:
ADL = Acid Detergent Lignin, % of dry matter
LSD = Least Significant Difference
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 17

Whole plant hay ADL measurements for the 6 reduced lignin alfalfa lead events in fall dormant (FD) germplasms grown in 4 locations in 2009

| Event | Event Mean | Control Mean | Delta | Delta LCI @ 90% | Delta UCI @ 90% | % Diff. | P-value |
|---|---|---|---|---|---|---|---|
| JJ041 | 4.93 | 5.77 | −0.85 | −1.07 | −0.62 | −14.64 | <0.001 |
| JJ266 | 4.66 | 5.77 | −1.11 | −1.33 | −0.89 | −19.25 | <0.001 |
| KK136 | 5.12 | 5.77 | −0.65 | −0.88 | −0.43 | −11.34 | <0.001 |
| KK179 | 5.23 | 5.77 | −0.54 | −0.77 | −0.32 | −9.41 | <0.001 |
| KK376 | 4.61 | 5.77 | −1.16 | −1.39 | −0.93 | −20.09 | <0.001 |
| KK465 | 5.28 | 5.77 | −0.49 | −0.71 | −0.26 | −8.43 | <0.001 |

Abbreviations used in the tables that follow:
ADL = Acid Detergent Lignin, % of dry matter
LSD = Least Significant Difference
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed 5 test for significance).

Whole plant ADL data from 2009 across 4 locations is shown in Table 17 and 19. The 6 reduced lignin positive events in fall dormant germplasm showed a significant (p≤0.05) decrease in ADL ranging from 8-19% when compared to the pooled negative control. Event KK179-2 had a 9.8% and a 9.45 reduction in ADL in the fall dormancy germplasms respectively.

TABLE 18

Whole plant hay ADL measurements for the 6 reduced lignin alfalfa lead events in non dormant (ND) germplasms grown in 2 locations in 2009

| Event | Event Mean | Control Mean | Delta | Delta LCI @ 90% | Delta UCI @ 90% | % Diff. | P-value |
|---|---|---|---|---|---|---|---|
| JJ041 | 5.25 | 5.94 | −0.69 | −1.10 | −0.28 | −11.59 | 0.006 |
| JJ266 | 4.86 | 5.94 | −1.08 | −1.48 | −0.69 | −18.21 | <0.001 |
| KK136 | 5.57 | 5.94 | −0.37 | −0.76 | −0.02 | −6.22 | 0.123 |
| KK179 | 5.29 | 5.94 | −0.65 | −1.04 | −0.25 | −10.91 | 0.007 |
| KK376 | 5.02 | 5.94 | −0.92 | −1.33 | −0.51 | −15.47 | <0.001 |
| KK465 | 5.37 | 5.94 | −0.57 | −0.96 | −0.18 | −9.61 | 0.018 |

Abbreviations used in the tables that follow:
ADL = Acid Detergent Lignin, % of dry matter
LSD = Least Significant Difference
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Whole plant ADL data from 2009 across 2 locations is shown in Table 18 and 20. The 6 reduced lignin positive events in the non dormant germplasm showed a significant (p≤0.05) decrease in ADL ranging from 10-16% when compared to the pooled negative control. Five of the 6 events showed a significant decrease in ADL ranging from 10-18% when compared to the pooled negative control. Event KK179-2 had 12.3% and 10.9% reduction in ADL in the non dormant germplasms respectively.

TABLE 19

Whole plant hay ADL measurements for the reduced lignin alfalfa event KK179-2 in two fall dormant (FD) germplasms grown in 4 locations in 2009 compared to commercial checks

| Commercial Check | Dormancy Germplasm | KK179 | Check Mean | Delta | Delta LCI @ 90% | Delta UCI @ 90% | % Diff. | P-value |
|---|---|---|---|---|---|---|---|---|
| 1 | FD1 | 5.22 | 6.12 | −0.90 | −1.19 | −0.62 | −14.77 | <.001 |
| 2 | FD1 | 5.22 | 5.69 | −0.47 | −0.76 | −0.18 | −8.31 | 0.008 |
| 3 | FD1 | 5.22 | 5.38 | −0.17 | −0.46 | 0.13 | −3.08 | 0.350 |
| 4 | FD1 | 5.22 | 5.59 | −0.38 | −0.67 | −0.09 | −6.75 | 0.034 |
| 1 | FD2 | 5.10 | 6.12 | −1.02 | −1.31 | −0.73 | −16.67 | <.001 |
| 2 | FD2 | 5.10 | 5.69 | −0.59 | −0.89 | −0.29 | −10.35 | 0.001 |
| 3 | FD2 | 5.10 | 5.38 | −0.28 | −0.58 | 0.02 | −5.24 | 0.119 |
| 4 | FD2 | 5.10 | 5.59 | −0.49 | −0.79 | −0.20 | −8.83 | 0.006 |

Abbreviations used in the tables that follow:
ADL = Acid Detergent Lignin, % of dry matter
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 20

Whole plant hay ADL measurements for the reduced lignin alfalfa event KK179-2 in two non dormant (ND) germplasm grown in 2 locations in 2009 compared to commercial checks

| Commercial Check | Germplasm | KK179-2 | Check Mean | Delta | Delta LCI @ 90% | Delta UCI @ 90% | % Diff. | P-value |
|---|---|---|---|---|---|---|---|---|
| 1 | ND1 | 5.29 | 5.73 | −0.44 | −0.96 | 0.09 | −7.62 | 0.173 |
| 2 | ND1 | 5.29 | 5.81 | −0.52 | −1.04 | 0.01 | −8.92 | 0.106 |
| 3 | ND1 | 5.29 | 5.77 | −0.48 | −1.01 | 0.05 | −8.34 | 0.133 |
| 4 | ND1 | 5.29 | 5.92 | −0.63 | −1.15 | −0.10 | −10.61 | 0.050 |
| 1 | ND2 | 5.39 | 5.73 | −0.33 | −0.88 | 0.21 | −5.77 | 0.318 |
| 2 | ND2 | 5.39 | 5.81 | −0.41 | −0.96 | 0.13 | −7.11 | 0.213 |
| 3 | ND2 | 5.39 | 5.77 | −0.38 | −0.92 | 0.17 | −6.51 | 0.257 |
| 4 | ND2 | 5.39 | 5.92 | −0.52 | −1.07 | 0.02 | −8.82 | 0.115 |

Abbreviations used in the tables that follow:
ADL = Acid Detergent Lignin, % of dry matter
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Tables 19 and 20 contain whole plant ADL data for the reduced lignin alfalfa event KK179-2 compared to commercial checks. The KK179-2 event showed a significant ($p \leq 0.1$) decrease in ADL when compared to 3 of the 4 fall dormant commercial checks which ranged from 6.8-16.7% (Table 19, data from 4 locations). KK179-2 event in non dormant background germplasm (ND1) showed a decrease ($p \leq 0.2$) in ADL compared to all 4 non dormant commercial checks ranging from 7.6-10.6% (Table 20, data from 2 locations). The KK179-2 event in non dormant background germplasm (ND2) showed a overall decrease ($p \leq 0.2$) in ADL compared to all 4 non dormant commercial checks with a significant ($p \leq 0.1$) decrease of 8.8% compared to commercial event 4 (ND2, data from 2 locations).

Example 7. NDFD Measurements in the Whole Plant for Reduced Lignin Alfalfa Events

TABLE 21

Whole plant hay NDFD measurements for the 6 reduced lignin alfalfa lead events in fall dormant (FD) germplasms grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 45.38 | 39.47 | 5.90 | 4.32 | 7.49 | 14.96 | <0.001 |
| JJ266 | 44.00 | 39.47 | 4.53 | 3.15 | 5.92 | 11.48 | <0.001 |
| KK136 | 43.92 | 39.47 | 4.45 | 2.80 | 6.10 | 11.27 | <0.001 |
| KK179 | 42.44 | 39.47 | 2.97 | 1.47 | 4.47 | 7.53 | 0.001 |
| KK376 | 44.82 | 39.47 | 5.35 | 3.71 | 6.99 | 13.55 | <0.001 |
| KK465 | 42.13 | 39.47 | 2.66 | 1.07 | 4.25 | 6.74 | 0.006 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 22

Whole plant hay NDFD measurements for the 6 reduced lignin alfalfa lead events in non dormant (ND) germplasms grown in 2 locations in 2009

| Event | Event Mean | Control Mean | Delta | Delta LCI @ 90% | Delta UCI @ 90% | % Diff. | P-value |
|---|---|---|---|---|---|---|---|
| JJ041 | 40.63 | 35.41 | 5.23 | 1.84 | 8.61 | 14.76 | 0.011 |
| JJ266 | 40.81 | 35.41 | 5.41 | 2.35 | 8.46 | 15.27 | 0.004 |
| KK136 | 38.66 | 35.41 | 3.25 | −0.19 | 6.70 | 9.19 | 0.120 |
| KK179 | 40.37 | 35.41 | 4.96 | 1.73 | 8.19 | 14.01 | 0.012 |
| KK376 | 39.75 | 35.41 | 4.35 | 0.96 | 7.73 | 12.28 | 0.035 |
| KK465 | 38.72 | 35.41 | 3.32 | 0.26 | 6.37 | 9.37 | 0.074 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 23

Whole plant hay NDFD measurements for the 6 reduced lignin alfalfa lead events in fall dormant (FD) germplasms grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 44.42 | 38.96 | 5.46 | 3.92 | 7.00 | 14.02 | <.001 |
| JJ266 | 45.19 | 38.96 | 6.22 | 4.72 | 7.73 | 15.98 | <.001 |
| KK136 | 43.63 | 38.96 | 4.66 | 3.16 | 6.17 | 11.97 | <.001 |
| KK179 | 42.56 | 38.96 | 3.60 | 2.10 | 5.10 | 9.24 | <.001 |
| KK376 | 45.41 | 38.96 | 6.45 | 4.90 | 7.99 | 16.54 | <.001 |
| KK465 | 41.52 | 38.96 | 2.55 | 1.05 | 4.06 | 6.55 | 0.005 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
FD = Fall Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10

TABLE 23-continued

Whole plant hay NDFD measurements for the 6 reduced lignin alfalfa lead events in fall dormant (FD) germplasms grown in 4 locations in 2009.

| Event | Event Mean | Control Mean | Delta | Delta LCI @ 90% | Delta UCI @ 90% | % Diff. | P-value |
|---|---|---|---|---|---|---|---|

Delta UCI @ 90% = Upper Confidence Interval of Delta value using an alpha level of 0.10
P-value = probability of a greater absolute difference under the null hypothesis (2-tailed test for significance).

Whole plant NDFD data from 2009 across 4 locations is shown in Table 23 and 25. The 6 reduced lignin positive events in fall dormant germplasm showed a significant (p≤0.05) increase in NDFD ranging from 7-16% when compared to the pooled negative control. Event KK179-2 had a 7.5% and 9.2% increase in NDFD in the fall dormant germplasm respectively.

TABLE 24

Whole plant hay NDFD measurements for the 6 reduced lignin alfalfa lead events in non dormant (ND) germplasms grown in 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 40.95 | 37.21 | 3.74 | 0.68 | 6.81 | 10.06 | 0.045 |
| JJ266 | 42.06 | 37.21 | 4.85 | 1.92 | 7.79 | 13.05 | 0.007 |
| KK136 | 40.24 | 37.21 | 3.03 | 0.10 | 5.97 | 8.15 | 0.089 |
| KK179 | 41.48 | 37.21 | 4.27 | 1.34 | 7.21 | 11.49 | 0.017 |
| KK376 | 42.22 | 37.21 | 5.01 | 1.95 | 8.08 | 13.47 | 0.007 |
| KK465 | 40.35 | 37.21 | 3.15 | 0.21 | 6.08 | 8.46 | 0.078 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Whole plant NDFD data from 2009 across 2 locations is shown in Table 24 and 26. The 6 reduced lignin positive events in non dormant germplasm showed a significant (p≤0.1) increase in NDFD ranging from 8-15% when compared to the pooled negative control. Event KK179-2 had a 14.0% and 11.5% increase in NDFD in the non dormant germplasm respectively.

TABLE 25

Whole plant hay NDFD measurements for the reduced lignin alfalfa event KK179-2 in two fall dormant (FD) germplasms grown in 4 locations in 2009 compared to commercial checks

| Commercial Check | Germplasm | KK179 | Check Mean | Delta | Delta LCI @ 90% | Delta UCI @ 90% | % Diff. | P-value |
|---|---|---|---|---|---|---|---|---|
| 1 | FD1 | 42.17 | 36.10 | 6.07 | 4.27 | 7.86 | 16.80 | <.001 |
| 2 | FD1 | 42.17 | 40.34 | 1.83 | 0.00 | 3.66 | 4.53 | 0.101 |
| 3 | FD1 | 42.17 | 41.27 | 0.89 | −0.94 | 2.72 | 2.16 | 0.423 |
| 4 | FD1 | 42.17 | 38.87 | 3.29 | 1.46 | 5.12 | 8.47 | 0.003 |
| 1 | FD2 | 42.03 | 36.10 | 5.93 | 4.11 | 7.76 | 16.44 | <.001 |
| 2 | FD2 | 42.03 | 40.34 | 1.70 | −0.17 | 3.56 | 4.21 | 0.134 |
| 3 | FD2 | 42.03 | 41.27 | 0.76 | −1.10 | 2.63 | 1.84 | 0.502 |
| 4 | FD2 | 42.03 | 38.87 | 3.16 | 1.30 | 5.03 | 8.13 | 0.005 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
FD = Fall Dormant
KK179 = KK179-2 reduced lignin alfalfa lead event

TABLE 25-continued

Whole plant hay NDFD measurements for the reduced lignin alfalfa event KK179-2 in two fall dormant (FD) germplasms grown in 4 locations in 2009 compared to commercial checks

| Commercial Check | Germplasm | KK179 | Check Mean | Delta | Delta LCI @ 90% | Delta UCI @ 90% | % Diff. | P-value |
|---|---|---|---|---|---|---|---|---|

Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

TABLE 26

Whole plant hay NDFD measurements for the reduced lignin alfalfa event KK179-2 in two non dormant (ND) germplasm grown in 2 locations in 2009 compared to commercial checks

| Commercial Check | Germplasm | KK179 | Check Mean | Delta | Delta LCI @ 90% | Delta UCI @ 90% | % Diff. | P-value |
|---|---|---|---|---|---|---|---|---|
| 1 | ND1 | 41.46 | 37.77 | 3.68 | −0.27 | 7.64 | 9.75 | 0.126 |
| 2 | ND1 | 41.46 | 37.12 | 4.34 | 0.39 | 8.30 | 11.70 | 0.071 |
| 3 | ND1 | 41.46 | 34.71 | 6.74 | 2.79 | 10.70 | 19.43 | 0.005 |
| 4 | ND1 | 41.46 | 35.70 | 5.75 | 1.80 | 9.71 | 16.12 | 0.017 |
| 1 | ND2 | 40.38 | 37.77 | 2.60 | −1.49 | 6.70 | 6.89 | 0.296 |
| 2 | ND2 | 40.38 | 37.12 | 3.26 | −0.84 | 7.36 | 8.79 | 0.190 |
| 3 | ND2 | 40.38 | 34.71 | 5.66 | 1.57 | 9.76 | 16.31 | 0.023 |
| 4 | ND2 | 40.38 | 35.70 | 4.67 | 0.58 | 8.77 | 13.09 | 0.061 |

Abbreviations used in the tables that follow:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter))
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Tables 25 and 26 contain whole plant NDFD data for the reduced lignin alfalfa event KK179-2 compared to commercial checks. The KK179-2 event showed an increase (p≤0.2) in NDFD when compared to 3 of the 4 fall dormant commercial checks which ranged from 4.2-16.8% (Table 25, data from 4 locations). KK179-2 event showed an increase (p≤0.2) in NDFD compared to all 4 non dormant commercial checks (ND1) ranging from 9.8-19.4% (Table 26, data from 2 locations). The KK179-2 event showed an increase (p≤0.2) in NDFD compared to all 4 non dormant commercial checks (ND2), which ranged from 8.8-16.3% (Table 26, data from 2 locations).

Example 8

Example 8: Yield Across Location Analysis for Reduced Lignin Alfalfa Events

TABLE 27

Yield across location analysis for 6 reduced lignin events for in fall dormant (FD) and non-dormant (ND) backgrounds compared to pooled negative controls

| Event | Dormancy germplasm | Year | Event Mean | Control Mean | Delta | Delta LCI @ 90% | Delta UCI @ 90% | % Diff. | P-value |
|---|---|---|---|---|---|---|---|---|---|
| JJ041 | FD | 2008 | 337.56 | 349.32 | −11.76 | −42.86 | 19.35 | −3.37 | 0.532 |
| JJ266 | FD | 2008 | 364.72 | 349.32 | 15.40 | −12.94 | 43.74 | 4.41 | 0.370 |
| KK136 | FD | 2008 | 306.67 | 349.32 | −42.65 | −78.12 | −7.19 | −12.21 | 0.048 |
| KK179 | FD | 2008 | 368.51 | 349.32 | 19.19 | −11.91 | 50.30 | 5.49 | 0.309 |
| KK376 | FD | 2008 | 354.92 | 349.32 | 5.60 | −29.85 | 41.05 | 1.60 | 0.794 |
| KK465 | FD | 2008 | 358.74 | 349.32 | 9.42 | −21.68 | 40.53 | 2.70 | 0.617 |
| JJ041 | FD | 2009 | 1148.41 | 1591.58 | −143.17 | −278.80 | −7.55 | −9.00 | 0.083 |
| JJ266 | FD | 2009 | 156.50 | 1591.58 | −26.08 | −147.97 | 95.82 | −1.64 | 0.724 |
| KK136 | FD | 2009 | 1468.30 | 1591.58 | −123.28 | −269.17 | 22.61 | −7.75 | 0.164 |
| KK179 | FD | 2009 | 1577.84 | 1591.58 | −13.74 | −145.29 | 117.81 | −0.86 | 0.863 |
| KK376 | FD | 2009 | 1371.19 | 1591.58 | −220.39 | −361.43 | −79.35 | −13.85 | 0.011 |

TABLE 27-continued

Yield across location analysis for 6 reduced lignin events for in fall dormant (FD) and non-dormant (ND) backgrounds compared to pooled negative controls

| Event | Dormancy germplasm | Year | Event Mean | Control Mean | Delta | Delta LCI @ 90% | Delta UCI @ 90% | % Diff. | P-value |
|---|---|---|---|---|---|---|---|---|---|
| KK465 | FD | 2009 | 1459.44 | 1591.58 | −132.14 | −272.37 | 8.09 | −8.30 | 0.121 |
| JJ041 | ND | 2009 | 591.17 | 764.86 | −173.70 | −292.96 | −54.43 | −22.71 | 0.018 |
| JJ266 | ND | 2009 | 758.32 | 764.86 | −6.54 | −119.09 | 106.01 | −0.86 | 0.923 |
| KK136 | ND | 2009 | 771.81 | 764.86 | 6.95 | −121.20 | 135.10 | 0.91 | 0.928 |
| KK179 | ND | 2009 | 754.11 | 764.86 | −10.75 | −130.04 | 108.54 | −1.41 | 0.881 |
| KK376 | ND | 2009 | 584.31 | 764.86 | −180.55 | −299.84 | −61.25 | −23.61 | 0.014 |
| KK465 | ND | 2009 | 637.67 | 764.86 | −127.20 | −239.75 | −14.65 | −16.63 | 0.064 |

Abbreviations used in the tables that follow:
Yield = Yield calculated on a per plant basis in grams
FD = Fall Dormant
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

The data in Table 27 shows the across location yield analysis for the 6 reduced lignin events in the fall dormant (FD) and non dormant (ND) germplasms compared to the pooled negative control. There were no significant decrease in yield is detected for KK179-2 when compared to the pooled negative controls.

TABLE 28

Yield across location analysis for Event KK179-2 compared to commercial checks

| Commerical Check | Dormancy germplasm | Year | Event Mean | Control Mean | Delta | LCI @ 90% | Delta UCI @ 90% | % Diff. | P-value |
|---|---|---|---|---|---|---|---|---|---|
| 1 | FD | 2008 | 368.51 | 239.29 | 129.22 | 92.13 | 166.31 | 54.00 | <.001 |
| 2 | FD | 2008 | 368.51 | 308.06 | 60.45 | 23.35 | 97.54 | 19.62 | 0.008 |
| 3 | FD | 2008 | 368.51 | 349.47 | 19.05 | −18.05 | 56.14 | 5.45 | 0.397 |
| 4 | FD | 2008 | 368.51 | 301.09 | 67.42 | 30.33 | 104.51 | 22.39 | 0.003 |
| 1 | FD | 2009 | 1361.60 | 1106.96 | 254.64 | 112.59 | 396.69 | 23.00 | 0.003 |
| 2 | FD | 2009 | 1361.60 | 1289.66 | 71.94 | −72.74 | 216.62 | 5.58 | 0.412 |
| 3 | FD | 2009 | 1361.60 | 1396.58 | −34.99 | −179.66 | 109.69 | −2.51 | 0.690 |
| 4 | FD | 2009 | 1361.60 | 1225.01 | 136.59 | −8.09 | 281.27 | 11.15 | 0.120 |
| 5 | ND | 2009 | 752.63 | 735.61 | 17.03 | −95.75 | 129.80 | 2.31 | 0.802 |
| 6 | ND | 2009 | 752.63 | 803.99 | −51.36 | −164.13 | 61.42 | −6.39 | 0.451 |
| 7 | ND | 2009 | 752.63 | 698.51 | 54.12 | −58.66 | 166.89 | 7.75 | 0.427 |
| 8 | ND | 2009 | 752.63 | 618.75 | 133.89 | 21.11 | 246.66 | 21.64 | 0.052 |

Abbreviations used in the tables that follow:
Yield = Yield calculated on a per plant basis in grams
FD = Fall Dormant
ND = Non Dormant
KK179 = KK179-2 reduced lignin alfalfa lead event
Delta = difference between Event and Control means (Event − Control)
% Diff = Percent difference between Event and Control (Delta/Control * 100)
Delta LCI @ 90% = Lower Confidence Interval of Delta value using an alpha level of 0.10
Delta UCI @ 90% = Upper Confidence Interval of Delta value using an alpha level of 0.10
P-value = probability of a greater absolute difference under the null hypothesis (2-tailed test for significance).

Yield data for reduced lignin alfalfa lead event in fall dormant (FD) and non-dormant (ND) germplasms resulted in no significant yield decrease when compared to 8 commercial checks.

---

We claim:

1. A seed of an alfalfa plant comprising event KK179-2, wherein representative seed comprising said event have been deposited with the American Type Culture Collection (ATCC) with the Patent Deposit Designation PTA-11833.

2. An alfalfa plant comprising event KK179-2 produced by growing the seed of claim 1, or a part thereof comprising said event.

3. The alfalfa plant KK179-2 or part thereof of claim 2, wherein the part comprises pollen, ovule, flowers, shoots, roots or leaves.

4. A progeny plant or a part thereof of the alfalfa plant of claim 2, wherein said progeny plant or parts thereof comprise said event KK179-2.

5. The progeny plant or part thereof of claim 4, wherein the part comprises pollen, ovule, flowers, shoots, roots or leaves.

6. A recombinant DNA molecule comprising a polynucleotide molecule selected from the group consisting of SEQ ID NO: 1, SEQ ID NO: 2, SEQ ID NO:3, SEQ ID NO:4 and SEQ ID NO:6, or a polynucleotide complementary thereto.

7. The DNA molecule of claim 6, wherein said DNA molecule comprises SEQ ID NO:1 and SEQ ID NO:2.

8. The DNA molecule of claim 6, wherein said DNA molecule comprises SEQ ID NO:3 and SEQ ID NO:4.

9. A microorganism comprising the DNA molecule of claim 6.

10. The microorganism of claim 9, wherein said microorganism is a plant cell.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial sequence

```
<220> FEATURE:
<221> NAME/KEY: misc_feature
<222> LOCATION: (1)..(20)
<223> OTHER INFORMATION: 5' Junction Sequence

<400> SEQUENCE: 1
gataataatc ttcaattgta                                              20

<210> SEQ ID NO 2
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: 3' Junction sequence

<400> SEQUENCE: 2
cccgccttca aaacctcttt                                              20

<210> SEQ ID NO 3
<211> LENGTH: 1147
<212> TYPE: DNA
<213> ORGANISM: Artificial sequence
<220> FEATURE:
<221> NAME/KEY: misc_feature
<222> LOCATION: (1)..(1147)
<223> OTHER INFORMATION: 5' Flanking Sequence Plus Junction

<400> SEQUENCE: 3
tgtcatacaa aataataatt gtggtatggg aatttgaaga atcagtaatt cttttttgata   60
tatatataat atatatggaa aaatgtaata tactcgtata cgggccggcc tggtaggctt  120
gataggcttt tttataagcc taagtctgac ctaattaaat taataggctt tttaaaaagc  180
tcaagcttga cccatttatt aaacaagtta ggtcaagccg ggcttttagt aggccgagcc  240
ataggcccct gacgagcggc ttgacctatt cccacccccta aggaacttat taaagaaata  300
tacacataaa aagtcgtgca ttcaacttct taaaagttaa tataatatat tttccaatgc  360
aaagttgcct ttttttgggtt gcttaacata tgcccttagg gcacaagtta acatgaccct  420
ggactattag tcttgactat aacttttgaa tgtcgttgag atttatattt gaattgtagc  480
ttttaatta ttagttttta gtcaagtaat tgttgctttt tatttaatt gggcttagtc    540
atctttttg tctgaaatat gattttcggt gaaatagac tttaataatc taaaatttgg     600
ttgaaagata aatataatat ggtccataat tatttcggtc atgatttata cttgaattct  660
cttaaatggt ttgttcataa ctaaagttca ttcaacactt ggtctcaaac ggttattgtt  720
atcatggttt tacaatattc atattaatat aattgttttc ctttcttcat tggaacaata  780
aaaataaggg tcttgctaac aagtgctcta agggcattgt ttaaggaacc caaaaaaga   840
aactatgtct tgaaaataca agtcaaacac ttttaaaagt cataaccgga caatttccaa  900
tgcaaaaatt gctactttta tatgcttaaa caatgcccct agggcacttg ttagcatttt  960
cctaaaaata atagatacag ttgaaatcgt atttgaaatt aattaagtag atatttaaat 1020
cgaatcaaac cacaattgat aataatcttc aattgtaaat ggcttcatgt ccgggaaatc 1080
tacatggatc agcaatgagt atgatggtca atatggagaa aagaaagag taattaccaa  1140
tttttttt                                                          1147

<210> SEQ ID NO 4
<211> LENGTH: 1356
<212> TYPE: DNA
```

<210> SEQ ID NO 4
<211> LENGTH: 1356
<212> TYPE: DNA
<213> ORGANISM: Artificial sequence
<220> FEATURE:
<221> NAME/KEY: misc_feature
<222> LOCATION: (1)..(1356)
<223> OTHER INFORMATION: 3' Flaking Sequence Plus Junction

<400> SEQUENCE: 4

```
gtgtcatcta tgttactaga tcgggaattc cccgcggccg ctcgagcagg acctgcagaa    60
gctagcttga tggggatcag attgtcgttt cccgccttca aaacctcttt taatcttcga   120
tatcttactt tagcctagtt acttttaaaa aagattcagg taaatcaaat atttcatgtg   180
attaattttc atacattgac aatgtaattt tttttacaca tgcatccaac cacatcacgt   240
taaatagaaa atttcacgaa atctaaaaat aatatctcgc caattatcca ttttctatga   300
aaatatcact tgccattaaa tacaactgca aacattacaa aaagttgttt aaagacaaat   360
tacgtacact tagacttgtt gcacaaaagg aaaagtaaag aaatataaga cgccttttag   420
acgcattcaa atgaacaata catattatag gacaataata gtggcacaaa taacttatta   480
gcaccactac cttaaaaaaa aaaacttatt agcaccacta aaaactcttt agatttgagc   540
taaacgatta atatcaatag ggtaagcatc tgatgcagat tgagcattgt aagctcttct   600
accaataaca ctatttccag cttcagttgg atgaaatgca tcccaaaata agaacccatt   660
cctatcccta catgcaggtt gaaagggcaa acatgtaatt tgaccattgt ttcttcctac   720
accacagcat ccagcatttg taactctaaa acctgaaaat tagaaagaaa aaaaaattat   780
tttgataact tgaaaaattg atgaattgtg aatttaaatt attttaggga gaaaataatt   840
accataggat gatgggctgg ttatgatgtc ttgaaagata ccataaacat ttacatagat   900
gaatcttgca tcaggaagtt ggttattgag ttgatcaaca agagatctta atccattgtt   960
gaataattga tttgcagaat tgattcttgc tacacatgtt ctaccatctg ggctgttttg  1020
agccaatgca tttggggtac aacctatttg accaactcca aataacgcca ttttccttgc  1080
cccataatta tataaaatct gaatcacaaa cacaacaatt gaacaacttt taaggacatt  1140
agcatatata aaaatttcaa ttaccaaagg acagtgtccc aattgtaaaa ttaaattgtt  1200
attaatgatt attttacgac cgtctctctg atgaaaaaat atataaacaa aaagtacat  1260
atagagaaag agtctgaccc taagttgctg agcatatgct tgaagaagga cattagcata  1320
ttgttgtggt gtgaattgtc tacttgtaga atagat                            1356
```

<210> SEQ ID NO 5
<211> LENGTH: 2582
<212> TYPE: DNA
<213> ORGANISM: Artificial sequence
<220> FEATURE:
<221> NAME/KEY: misc_feature
<222> LOCATION: (1)..(2582)
<223> OTHER INFORMATION: Transgene cassette with partial right border and full left border sequence.

<400> SEQUENCE: 5

```
ttcaattgta aatggcttca tgtccgggaa atctacatgg atcagcaatg agtatgatgg    60
tcaatatgga gaaaagaaa gagtaattac caatttttttt tcaattcaaa aatgtagatg   120
tccgcagcgt tattataaaa tgaaagtaca ttttgataaa acgacaaatt acgatccgtc   180
gtatttatag gcgaaagcaa taaacaaatt attctaattc ggaaatcttt atttcgacgt   240
gtctacattc acgtccaaat gggggcttag atgagaaact tcacgatttg gcgcgccaaa   300
gcttggtacc gaattcgagc tcgaaaagtc taagccaata ttcattattt tttatttatg   360
```

|  |  |
|---|---|
| cttaacattt atgttcaagc caatagtaac aagaagatga actggttttg tatattaatt | 420 |
| caatataacc aatccctgtg gagtgattta gttgaaagga tctacaattc taaagatgat | 480 |
| gagttaaacc ctagccgaag ttgtagttga atcttaaact tacttttcta aatagtaaca | 540 |
| cctgccataa atactagctg catcttaatt tctctacctc ccccacactc tggcatggcg | 600 |
| gccctgtcgt tttcttgctc catttttttt tctattatca cactttttct tttcatttct | 660 |
| ttcttgttat ctgtaaatcc gtgtcctttc ttcaagtaa ttactaaaac aaatgctaaa | 720 |
| gaaacacatt tatttattta tttttatctt tctaaccta tttaaccagt tttagaagcc | 780 |
| aattcccagg aatcatagtt cactttaact atgttttttt ttagtgagaa aagacaaaa | 840 |
| gatgaatgat tggttgcgat tccttgccct tttgttcttc ttatatatat atatatatat | 900 |
| atatatatat atatataccct agaaaagata atatgtacgt tgaaatcttt gttaaaagga | 960 |
| accagaaaat gtaaggatta ggaatttaat ttcgtagttg ggtaacattt attaattaat | 1020 |
| caattaatta attaattgat tgattttatac gtctatcttc tattccacgt cctgtgttgg | 1080 |
| tagggaagta cagagaagtt aggttctagt ccacaaggtg acatcgcacc cagagaaggg | 1140 |
| gagaaaaaat gccacgtcgc gcaatgagag ccgctgatgc aggctggtaa tccaacgctt | 1200 |
| gtcattattt ctccaccaac cccccttcact tcccccttgtg catcgttacc acccttttata | 1260 |
| cccacctacc agacaccaac gctccagatt tgcttcggcc ctaacactct ccgttatata | 1320 |
| taaccccttc atgaacaagg ctaatcattc accacattac gcactacttt tcctctctcc | 1380 |
| gtctcctcat tccttcattt ccggggatct cgcggatcct aacatacttc ctcaatggag | 1440 |
| catcagggg tgcaaccaca gatccattcc ataaggtgtt gtcgtacccg atcacacctc | 1500 |
| ccactttaac aagatcaatt aacctcttat ggtagttgag gtaattgtct ttgtcagcat | 1560 |
| ccacaaaaat gaaatcgtag ctaccatgat tcttttcgtc tttgatcatt tcatcaagaa | 1620 |
| ctggaagagc tggaccttct ctgaaatcaa ttttgtgatc aacaccagct tttttaatta | 1680 |
| caggtagacc caattcgtaa ttttctttgt taatgtccat agccaaaatc tttccatctt | 1740 |
| caggaatagc tagggcagtg gcaaggaggg agtagccagt gtagacacca atttccatgg | 1800 |
| tattcttagc attgataagt ttaaggagca tgctcaaaaa ttgtccttca tctgcagagg | 1860 |
| ttgtcatgat gttccatggg tgttttgctg tgacctctct caactctttc atggcttcat | 1920 |
| gttctcttgg gaagacatct agagtctaca ctggctactc cctccttgcc actgccctag | 1980 |
| ctattcctga agatggaaag attttggcta tggacattaa caaagaaaat tacgaattgg | 2040 |
| gtctacctgt aattaaaaaa gctggtgttg atcacaaaat tgatttcaga gaaggtccag | 2100 |
| ctcttccagt tcttgatgaa atgatcaaag acgaaaagaa tcatggtagc tacgatttca | 2160 |
| tttttgtgga tgctgacaaa gacaattacc tcaactacca taagaggtta attgatcttg | 2220 |
| ttaaagtggg aggtgtgatc gggccgcggc cgatcgttca aacatttggc aataaagttt | 2280 |
| cttaagattg aatcctgttg ccggtcttgc gatgattatc atataatttc tgttgaatta | 2340 |
| cgttaagcat gtaataatta acatgtaatg catgacgtta tttatgagat gggtttttat | 2400 |
| gattagagtc ccgcaattat acatttaata cgcgatagaa aacaaaatat agcgcgcaaa | 2460 |
| ctaggataaa ttatcgcgcg cggtgtcatc tatgttacta gatcgggaat tccccgcggc | 2520 |
| cgctcgagca ggacctgcag aagctagctt gatggggatc agattgtcgt ttcccgcctt | 2580 |
| ca | 2582 |

<210> SEQ ID NO 6
<211> LENGTH: 4885

<212> TYPE: DNA
<213> ORGANISM: Artificial sequence
<220> FEATURE:
<221> NAME/KEY: misc_feature
<222> LOCATION: (1)..(4885)
<223> OTHER INFORMATION: Contig of 5' flanking sequence, inserted DNA
      and 3' Flanking Sequence

<400> SEQUENCE: 6

| | | | | | |
|---|---|---|---|---|---|
| tgtcatacaa | aataataatt | gtggtatggg | aatttgaaga | atcagtaatt | cttttttgata | 60 |
| tatatataat | atatatggaa | aaatgtaata | tactcgtata | cgggccggcc | tggtaggctt | 120 |
| gataggcttt | tttataagcc | taagtctgac | ctaattaaat | taataggctt | tttaaaaagc | 180 |
| tcaagcttga | cccatttatt | aaacaagtta | ggtcaagccg | ggcttttagt | aggccgagcc | 240 |
| ataggcccct | gacgagcggc | ttgacctatt | cccaccccta | aggaacttat | taaagaaata | 300 |
| tacacataaa | aagtcgtgca | ttcaacttct | taaaagttaa | tataatatat | tttccaatgc | 360 |
| aaagttgcct | tttttgggtt | gcttaacata | tgcccttagg | gcacaagtta | acatgaccct | 420 |
| ggactattag | tcttgactat | aacttttgaa | tgtcgttgag | atttatattt | gaattgtagc | 480 |
| tttttaatta | ttagttttta | gtcaagtaat | tgttgctttt | tattttaatt | gggcttagtc | 540 |
| atctttttg | tctgaaatat | gattttcggt | gaaaatagac | tttaataatc | taaaatttgg | 600 |
| ttgaaagata | aatataatat | ggtccataat | tatttcggtc | atgatttata | cttgaattct | 660 |
| cttaaatggt | ttgttcataa | ctaaagttca | ttcaacactt | ggtctcaaac | ggttattgtt | 720 |
| atcatggttt | tacaatattc | atattaatat | aattgttttc | ctttcttcat | tggaacaata | 780 |
| aaaataaggt | tcttgctaac | aagtgctcta | agggcattgt | ttaaggaacc | caaaaaaga | 840 |
| aactatgtct | tgaaaataca | agtcaaacac | ttttaaaagt | cataaccgga | caatttccaa | 900 |
| tgcaaaaatt | gctacttta | tatgcttaaa | caatgccctt | agggcacttg | ttagcatttt | 960 |
| cctaaaaata | atagatacag | ttgaaatcgt | atttgaaatt | aattaagtag | atatttaaat | 1020 |
| cgaatcaaac | cacaattgat | aataatcttc | aattgtaaat | ggcttcatgt | ccgggaaatc | 1080 |
| tacatggatc | agcaatgagt | atgatggtca | atatggagaa | aaagaaagag | taattaccaa | 1140 |
| ttttttttca | attcaaaaat | gtagatgtcc | gcagcgttat | tataaaatga | aagtacattt | 1200 |
| tgataaaacg | acaaattacg | atccgtcgta | tttataggcg | aaagcaataa | acaaattatt | 1260 |
| ctaattcgga | aatctttatt | tcgacgtgtc | tacattcacg | tccaaatggg | ggcttagatg | 1320 |
| agaaacttca | cgatttggcg | cgccaaagct | tggtaccgaa | ttcgagctcg | aaaagtctaa | 1380 |
| gccaatattc | attattttt | atttatgctt | aacatttatg | ttcaagccaa | tagtaacaag | 1440 |
| aagatgaact | ggttttgtat | attaattcaa | tataaccaat | ccctgtggag | tgatttagtt | 1500 |
| gaaaggatct | acaattctaa | agatgatgag | ttaaacccta | gccgaagttg | tagttgaatc | 1560 |
| ttaaacttac | ttttctaaat | agtaacacct | gccataaata | ctagctgcat | cttaatttct | 1620 |
| ctacctcccc | cacactctgg | catggcggcc | ctgtcgtttt | cttgctccat | tttttttct | 1680 |
| attatcacac | ttttttcttt | catttctttc | ttgttatctg | taaatccgtg | tcctttcttc | 1740 |
| taagtaatta | ctaaaacaaa | tgctaaagaa | acacatttat | ttatttattt | ttatctttct | 1800 |
| aaccctattt | aaccagtttt | agaagccaat | tcccaggaat | catagttcac | tttaactatg | 1860 |
| tttttttta | gtgagaagaa | gacaaaagat | gaatgattgg | ttgcgattcc | ttgccctttt | 1920 |
| gttcttctta | tatatatata | tatatatata | tatatatata | tataccctaga | aaagataata | 1980 |
| tgtacgttga | aatctttgtt | aaaaggaacc | agaaaatgta | aggattagga | atttaatttc | 2040 |
| gtagttgggt | aacatttatt | aattaatcaa | ttaattaatt | aattgattga | tttatacgtc | 2100 |

```
tatcttctat tccacgtcct gtgttggtag ggaagtacag agaagttagg ttctagtcca    2160
caaggtgaca tcgcacccag agaaggggag aaaaaatgcc acgtcgcgca atgagagccg    2220
ctgatgcagg ctggtaatcc aacgcttgtc attatttctc caccaacccc cttcacttcc    2280
ccttgtgcat cgttaccacc ctttataccc acctaccaga caccaacgct ccagatttgc    2340
ttcggcccta acactctccg ttatatataa ccccttcatg aacaaggcta atcattcacc    2400
acattacgca ctacttttcc tctctccgtc tcctcattcc ttcatttccg gggatctcgc    2460
ggatcctaac atacttcctc aatggagcat caggggggtgc aaccacagat ccattccata    2520
aggtgttgtc gtacccgatc acacctccca ctttaacaag atcaattaac ctcttatggt    2580
agttgaggta attgtctttg tcagcatcca caaaaatgaa atcgtagcta ccatgattct    2640
tttcgtcttt gatcatttca tcaagaactg aagagctgg accttctctg aaatcaattt    2700
tgtgatcaac accagctttt ttaattacag gtagacccaa ttcgtaattt tctttgttaa    2760
tgtccatagc caaaatcttt ccatcttcag gaatagctag ggcagtggca aggagggagt    2820
agccagtgta gacaccaatt tccatggtat tcttagcatt gataagttta aggagcatgc    2880
tcaaaaattg tccttcatct gcagaggttg tcatgatgtt ccatgggtgt tttgctgtga    2940
cctctctcaa ctctttcatg gcttcatgtt ctcttgggaa gacatctaga gtctacactg    3000
gctactccct ccttgccact gccctagcta ttcctgaaga tggaaagatt ttggctatgg    3060
acattaacaa agaaaattac gaattgggtc tacctgtaat taaaaaagct ggtgttgatc    3120
acaaaattga tttcagagaa ggtccagctc ttccagttct tgatgaaatg atcaaagacg    3180
aaaagaatca tggtagctac gatttcattt ttgtggatgc tgacaaagac aattacctca    3240
actaccataa gaggttaatt gatcttgtta agtgggagg tgtgatcggg ccgcggccga    3300
tcgttcaaac atttggcaat aaagtttctt aagattgaat cctgttgccg gtcttgcgat    3360
gattatcata taatttctgt tgaattacgt taagcatgta ataattaaca tgtaatgcat    3420
gacgttattt atgagatggg tttttatgat tagagtcccg caattataca tttaatacgc    3480
gatagaaaac aaaatatagc gcgcaaacta ggataaatta tcgcgcgcgg tgtcatctat    3540
gttactagat cgggaattcc ccgcggccgc tcgagcagga cctgcagaag ctagcttgat    3600
ggggatcaga ttgtcgtttc ccgccttcaa aacctctttt aatcttcgat atcttacttt    3660
agcctagtta cttttaaaaa agattcaggt aaatcaaata tttcatgtga ttaattttca    3720
tacattgaca atgtaatttt ttttacacat gcatccaacc acatcacgtt aaatagaaaa    3780
tttcacgaaa tctaaaaata atatctcgcc aattatccat tttctatgaa atatcactt    3840 gccattaaat acaactgcaa acattacaaa aagttgttta agacaaaatt acgtacactt    3900
agacttgttg cacaaaagga aaagtaaaga aatataagac gccttttaga cgcattcaaa    3960
tgaacaatac atattatagg acaataatag tggcacaaat aacttattag caccactacc    4020
ttaaaaaaaa aaacttatta gcaccactaa aaactcttta gatttgagct aaacgattaa    4080
tatcaatagg gtaagcatct gatgcagatt gagcattgta agctcttcta ccaataacac    4140
tatttccagc ttcagttgga tgaaatgcat cccaaaataa gaacccattc ctatccctac    4200
atgcaggtta aagggcaaa catgtaattt gaccattgtt tcttcctaca ccacagcatc    4260
cagcatttgt aactctaaaa cctgaaaatt agaaagaaaa aaaaattatt ttgataactt    4320
gaaaaattga tgaattgtga atttaaatta ttttagggag aaaataatta ccataggatg    4380
atgggctggt tatgatgtct tgaaagatac cataaacatt tacatagatg aatcttgcat    4440
```

-continued

```
caggaagttg gttattgagt tgatcaacaa gagatcttaa tccattgttg aataattgat   4500
ttgcagaatt gattcttgct acacatgttc taccatctgg gctgttttga gccaatgcat   4560
ttggggtaca acctatttga ccaactccaa ataacgccat tttccttgcc ccataattat   4620
ataaaatctg aatcacaaac acaacaattg aacaactttt aaggacatta gcatatataa   4680
aaatttcaat taccaaagga cagtgtccca attgtaaaat taaattgtta ttaatgatta   4740
ttttacgacc gtctctctga tgaaaaaata tataaacaaa aaagtacata tagagaaaga   4800
gtctgaccct aagttgctga gcatatgctt gaagaaggac attagcatat tgttgtggtg   4860
tgaattgtct acttgtagaa tagat                                         4885
```

```
<210> SEQ ID NO 7
<211> LENGTH: 24
<212> TYPE: DNA
<213> ORGANISM: Artificial sequence
<220> FEATURE:
<221> NAME/KEY: misc_recomb
<222> LOCATION: (1)..(24)
<223> OTHER INFORMATION: Oligonucleotide primer SQ20901

<400> SEQUENCE: 7
cattgctgat ccatgtagat ttcc                                          24

<210> SEQ ID NO 8
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: Oligonucleotide primer SQ23728

<400> SEQUENCE: 8
aaatcgaatc aaaccacaat tgataat                                       27

<210> SEQ ID NO 9
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: 6FAM-labeled oligonucleotide probe PB10164

<400> SEQUENCE: 9
acatgaagcc atttacaatt                                               20

<210> SEQ ID NO 10
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Oligonucleotide primer SQ1532

<400> SEQUENCE: 10
ggtatccctc cagaccagca                                               20

<210> SEQ ID NO 11
<211> LENGTH: 24
<212> TYPE: DNA
<213> ORGANISM: Artificial sequence
<220> FEATURE:
<221> NAME/KEY: misc_feature
```

```
<222> LOCATION: (1)..(24)
<223> OTHER INFORMATION: Oligonucleotide primer SQ1533

<400> SEQUENCE: 11
gtggactcct tctggatgtt gtaa                                            24

<210> SEQ ID NO 12
<211> LENGTH: 29
<212> TYPE: DNA
<213> ORGANISM: Artificial sequence
<220> FEATURE:
<221> NAME/KEY: misc_feature
<222> LOCATION: (1)..(29)
<223> OTHER INFORMATION: VIC-labeled oligonucleotide probe PB0359

<400> SEQUENCE: 12
atatttgctg gaaagcagct tgaggatgg                                       29
```